US011648394B2

(12) United States Patent
Frank et al.

(10) Patent No.: US 11,648,394 B2
(45) Date of Patent: May 16, 2023

(54) METHODS OF IMPLANTING A DEVICE INTO A BRAIN

(71) Applicant: The Regents of the University of California, Oakland, CA (US)

(72) Inventors: Loren M. Frank, San Anselmo, CA (US); Jason Chung, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 229 days.

(21) Appl. No.: 16/756,013

(22) PCT Filed: Nov. 2, 2018

(86) PCT No.: PCT/US2018/059012
§ 371 (c)(1),
(2) Date: Apr. 14, 2020

(87) PCT Pub. No.: WO2019/090117
PCT Pub. Date: May 9, 2019

(65) Prior Publication Data
US 2021/0361935 A1  Nov. 25, 2021

Related U.S. Application Data

(60) Provisional application No. 62/581,437, filed on Nov. 3, 2017.

(51) Int. Cl.
| A61N 1/05 | (2006.01) |
| A61N 1/372 | (2006.01) |
| A61B 17/34 | (2006.01) |
| A61B 5/00 | (2006.01) |
| A61B 90/10 | (2016.01) |

(52) U.S. Cl.
CPC ........ *A61N 1/0531* (2013.01); *A61B 17/3468* (2013.01); *A61N 1/0539* (2013.01); *A61N 1/37223* (2013.01); *A61B 5/6868* (2013.01); *A61B 2090/103* (2016.02)

(58) Field of Classification Search
CPC ...... A61N 1/00; A61N 1/0531; A61N 1/0539; A61N 1/37223; A61B 17/3468; A61B 2090/103; A61B 5/6868
See application file for complete search history.

(56) References Cited

U.S. PATENT DOCUMENTS

| 3,755,042 A | 8/1973 | Robertson et al. |
| 4,144,317 A | 3/1979 | Higuchi et al. |
| 4,304,765 A | 8/1981 | Shell et al. |
| 4,482,053 A | 11/1984 | Alpern |
| 4,668,506 A | 5/1987 | Bawa |
| 4,750,619 A | 6/1988 | Cohen et al. |
| 4,846,191 A | 7/1989 | Brockway et al. |

(Continued)

OTHER PUBLICATIONS

Alexander (2009) "Remote control of neuronal activity in transgenic mice expressing evolved G protein-coupled receptors" Neuron Neurotechnique 63, 27-39.

(Continued)

*Primary Examiner* — Jon Eric C Morales
(74) *Attorney, Agent, or Firm* — Edward J. Baba; Bozicevic, Field & Francis LLP

(57) ABSTRACT

The present disclosure generally provides methods of implanting an implantable device in contact with a brain of a subject. Also provided are kits and systems for the implantation of one or more implantable devices.

45 Claims, 21 Drawing Sheets

(56) References Cited

U.S. PATENT DOCUMENTS

| | | | |
|---|---|---|---|
| 4,959,217 | A | 9/1990 | Sanders et al. |
| 5,658,329 | A | 8/1997 | Purkait |
| 5,824,074 | A | 10/1998 | Koch |
| 8,761,889 | B2 | 6/2014 | Wingeier et al. |
| 9,101,756 | B1 | 8/2015 | Pianca et al. |
| 2005/0268573 | A1 | 8/2005 | Yan |
| 2008/0103483 | A1 | 5/2008 | Johnson et al. |
| 2010/0133133 | A1 | 6/2010 | Hamas |
| 2011/0046470 | A1 | 2/2011 | Kipke et al. |

OTHER PUBLICATIONS

Bartha et al. (2004) "Characterization of neocortical principal cells and interneurons by network interactions and extracellular features" Journal Neurophysiology 92:600-608.

Bingzhao et al. (2018) "A nanofabricated optoelectronic probe for manipulating and recording neural dynamics" Journal Neural Engineering 15 (4).

Buzsaki (2004) "Large-scale recording of neuronal ensembles" Nature Neuroscience 7, 446-451.

Buzsaki (2015) "Hippocampal sharp wave-ripple: A cognitive biomarker for episodic memory and planning" Hippocampus 25, 1073-1188.

Chen et al. (2013) "Ultrasensitive fluorescent proteins for imaging neuronal activity" Nature 499, 295-300.

Cheng et al. (2008) "New experiences enhance coordinated neural activity in the hippocampus" Neuron 57, 303-313.

Chrobak et al. (1996) "High-frequency oscillations in the output networks of the hippocampal-entorhinal axis of the freely behaving rat" Journal of Neuroscience 16, 3056-3066.

Chung et al. (2017) "A Fully Automated Approach to Spike Sorting" Neuron 95, 1381-1394 e1386.

Dhawale et al. (2017) "Automated long-term recording and analysis of neural activity in behaving animals" eLife 6.

Dragoi et al. (1999) "Interactions between hippocampus and medial septum during sharp waves and theta oscillation in the behaving rat" Journal of Neuroscience 19, 6191-6199.

Encyclopedia of Polymer Science and Technology, vol. 3.

Felix et al. (2013) Insertion of flexible neural probes using rigid stiffeners attached with biodissolvable adhesive Journal of Visualized Experiments e50609.

Gilletti et al. (2006) "Brain micromotion around implants in the rodent somatosensory cortex" Journal Neural Engineering 3, 189-195.

Gray et al. (1995) "Tetrodes markedly improve the reliability and yield of multiple single-unit isolation from multi-unit recordings in cat striate cortex" Journal Neuroscience Methods 63, 43-54.

Greenberg et al. (2004) "Functional stability of dorsolateral prefrontal neurons" Journal Neurophysiology 92, 1042-1055.

Guehfnnec et al. (2007) "Surface treatments of titanium dental implants for rapid osseointegration" Dental Materials 23, 844-854.

Hengen et al. (2013) "Firing rate homeostasis in visual cortex of freely behaving rodents" Neuron 80, 335-342.

Hengen et al. (2016) "Neuronal firing rate homeostasis is inhibited by sleep and promoted by wake" Cell 165, 180-191.

Herbawi et al. (2017) "High-density Cmos neural probe implementing a hierarchical addressing scheme for 1600 recording sites and 32 output channels" 2017 19th International Conference on Solid-State Sensors, Actuators and Microsystems (Transducers), pp. 20-23.

Hromadka et al. (2008) "Sparse representation of sounds in the unanesthetized auditory cortex" PLoS Biology 6, e16.

Isomura et al. (2006) "Integration and segregation of activity in entorhinal-hippocampal subregions by neocortical slow oscillations" Neuron 52, 871-882.

Jadhav et al. (2016) "Coordinated excitation and inhibition of prefrontal ensembles during awake hippocampal sharp-wave ripple events" Neuron 90, 113-127.

Jeong et al. (2015) "Soft materials in neuroengineering for hard problems in neuroscience" Neuron 86(17), 5-186.

Ji et al. (2007) "Coordinated memory replay in the visual cortex and hippocampus during sleep" Nature Neuroscience 10, 100-107.

Jun et al. (2017) "Fully integrated silicon probes for high-density recording of neural activity" Nature 551, 232-236.

Kay et al. (2016) "A hippocampal network for spatial coding during immobility and sleep" Nature 531, 185-190.

Khodagholy et al. (2017) "Learning-enhanced coupling between ripple oscillations in association cortices and hippocampus" Science 358, 369-372.

Kim et al. (2013) "Injectable, cellular-scale optoelectronics with applications for wireless optogenetics" Science 340, 211-216.

Kim et al. (2003) "Control of degradation rate and hydrophilicity in electrospun non-woven poly(D,L-lactide) nanofiber scaffolds for biomedical applications" Biomaterials 24, (27), 4977-4985.

Kuo et al. (2013) "Novel flexible Parylene neural probe with 3D sheath structure for enhancing tissue integration" Lab Chip 13, 554-561.

Lansink et al. (2009) "Hippocampus leads ventral striatum in replay of place-reward information" PLoS Biol 7, e1000173.

Lee et al. (2017) "Histological evaluation of flexible neural implants; flexibility limit for reducing the tissue response" Journal Neural Engineering 14, 036026.

Lee et al. (2017) "Placing sites on the edge of planar silicon microelectrodes enhances chronic recording functionality" IEEE Transactions on Biomedical Engineering.

Logothetis et al. (2012) "Hippocampal-cortical interaction during periods of subcortical silence" Nature 491, 547-553.

Lopez et al. (2017) "A neural probe with up to 966 electrodes and up to 384 configurable channels in 0.13 mum SOI CMOS" IEEE Transactions on Biomedical Circuits and Systems 11(3), 510-522.

Luan et al. (2017) "Ultraflexible nanoelectronic probes form reliable, glial scar-free neural integration" Science Advances 3, 1-9.

Ludwig et al. (2006) "Chronic neural recordings using silicon microelectrode arrays electrochemically deposited with a poly(3,4-ethylenedioxythiophene) (PEDOT) film" Journal of Neural Engineering 3, 59-70.

Matsumura et al. (1988) "Adhesive 4-META/MMA-TBB opaque resin with poly(methyl methacrylate)-coated titanium dioxide" Journal of Dental Research 67, 29-32.

Mcmahon et al. (2014) "Face-selective neurons maintain consistent visual responses across months" Proceedings of the National Academy Science, 8251-8256.

Mizuseki et al. (2013) "Preconfigured, skewed distribution of firing rates in the hippocampus and entorhinal cortex" Cell Reports 4, 1010-1021.

Mols et al. (2017) "In vivo characterization of the electrophysiological and astrocytic responses to a silicon neuroprobe implanted in the mouse neocortex" Scientific Reports 7, 15642.

O'Connor et al. (2010) "Neural activity in barrel cortex underlying vibrissa-based object localization in mice" Neuron 67, 1048-1061.

Pennartz et al. (2004) "The ventral striatum in off-line processing: ensemble reactivation during sleep and modulation by hippocampal ripples" The Journal of Neuroscience 24, 6446-6456.

Pfeiffer et al. (2013) "Hippocampal place-cell sequences depict future paths to remembered goals" Nature 497, 74-79.

Pfeiffer (2015) "Autoassociative dynamics in the generation of sequences of hippocampal place cells" Science 349, 180-183.

Powell et al. (2014) "Complex neural codes in rat prelimbic cortex are stable across days on a spatial decision task" Frontiers in Behavioral Neuroscience 8, 120.

Raducanu et al. (2017) "Time multiplexed active neural probe with 1356 parallel recording sites" Sensors 17, 2388.

Rodger et al., (2008) "Flexible parylene-based multielectrode array technology for high-density neural stimulation and recording" Sensor Actuat B-Chem 132:449-460.

Roff et al. (1972) "Handbook of common polymers" CRC Press, Cleveland, Ohio.

Rose et al. (2016) "Cell-specific restoration of stimulus preference after monocular deprivation in the visual cortex" Science 352, 1319-1322.

Rosen et al. (1990) "Artificial nerve graft using collagen as an extracellular matrix for nerve repair compared with sutured autograft in a rat model" Annals of Plastic Surgery 25(5): 375-387.

(56) References Cited

OTHER PUBLICATIONS

Rothschild et al. (2017) "A cortical-hippocampal-cortical loop of information processing during memory consolidation" Nature Neuroscience 20, 251-259.
Rudmann, et al. (2018) "Integrated optoelectronic microprobes" Current Opinion in Neurobiology 50, 72-82.
Scholvin et al. (2016) "Close-packed silicon microelectrodes for scalable spatially oversampled neural recording" IEEE Transactions on Biomedical Engineering 63, 120-130.
Seo et al. (2015) "Model validation of untethered, ultrasonic neural dust motes for cortical recording" The Journal of Neuroscience Methods 244, 114-122.
Seo et al. (2016) "Wireless recording in the peripheral nervous system with ultrasonic neural dust" Neuron 91, 529-539.
Seymour et al. (2017) "State-of-the-art MEMS and microsystem tools for brain research" Microsystems &Amp; Nanoengineering 3, 16066.
Sirota et al. (2003) "Communication between neocortex and hippocampus during sleep in rodents" Proceedings of the National Academy of Sciences of the United States of America 100, 2065-2069.
Tang et al. (2017) "Hippocampal-prefrontal reactivation during learning is stronger in awake compared with sleep states" Journal of Neuroscience 37, 11789-11805.
Tooker et al. (2014) "Towards a large-scale recording system: demonstration of polymer-based penetrating array for chronic neural recording" Conf Proc IEEE Eng Med Biol Soc 2014, 6830-6833.
Tooker et al. (2013) "Microfabricated polymer-based neural interface for electrical stimulation/recording, drug delivery, and chemical sensing-development" IEEE Engineering in Medicine and Biology Society 5159-5162.
Tooker et al. (2012) "Optimization of multi-layer metal neural probe design" Annual International Conference of the IEEE Engineering in Medicine and Biology Society 5995-5998.
Tooker et al. (2012) "Polymer neural interface with dual-sided electrodes for neural stimulation and Recording" Annual International Conference of the IEEE Engineering in Medicine and Biology Society 5999-6002.
Wassum et al. (2008) "Silicon Wafer-Based Platinum Microelectrode Array Biosensor for Near Real-Time Measurement of Glutamate in Vivo" Sensors (Basel) 8, 5023-5036.
Wierzynski et al. (2009) "State-dependent spike-timing relationships between hippocampal and prefrontal circuits during sleep" Neuron 61, 587-596.
Wu et al. (2013) "An implantable neural probe with monolithically integrated dielectric waveguide and recording electrodes for optogenetics applications" Journal of Neural Engineering 10, 056012.
Xie et al. (2015) "Three-dimensional macroporous nanoelectronic networks as minimally invasive brain probes" Nature Materials 14, 1286-1292.
Yu et al. (2017) "Distinct hippocampal-cortical memory representations for experiences associated with movement versus immobility" eLife 6.
Zhao et al. (2017) "Nanoelectronic Coating Enabled Versatile Multifunctional Neural Probes" Nano letters 17, 4588-4595.
Zong et al. (2002) "Structure and process relationship of electrospun bioabsorbable nanofiber membranes" Polymer 43(16), 4403-4412.
Zong et al. (2005) "Electrospun fine-textured scaffolds for heart tissue constructs" Biomaterials 26, 5330-5338.

H

A

B

D

E

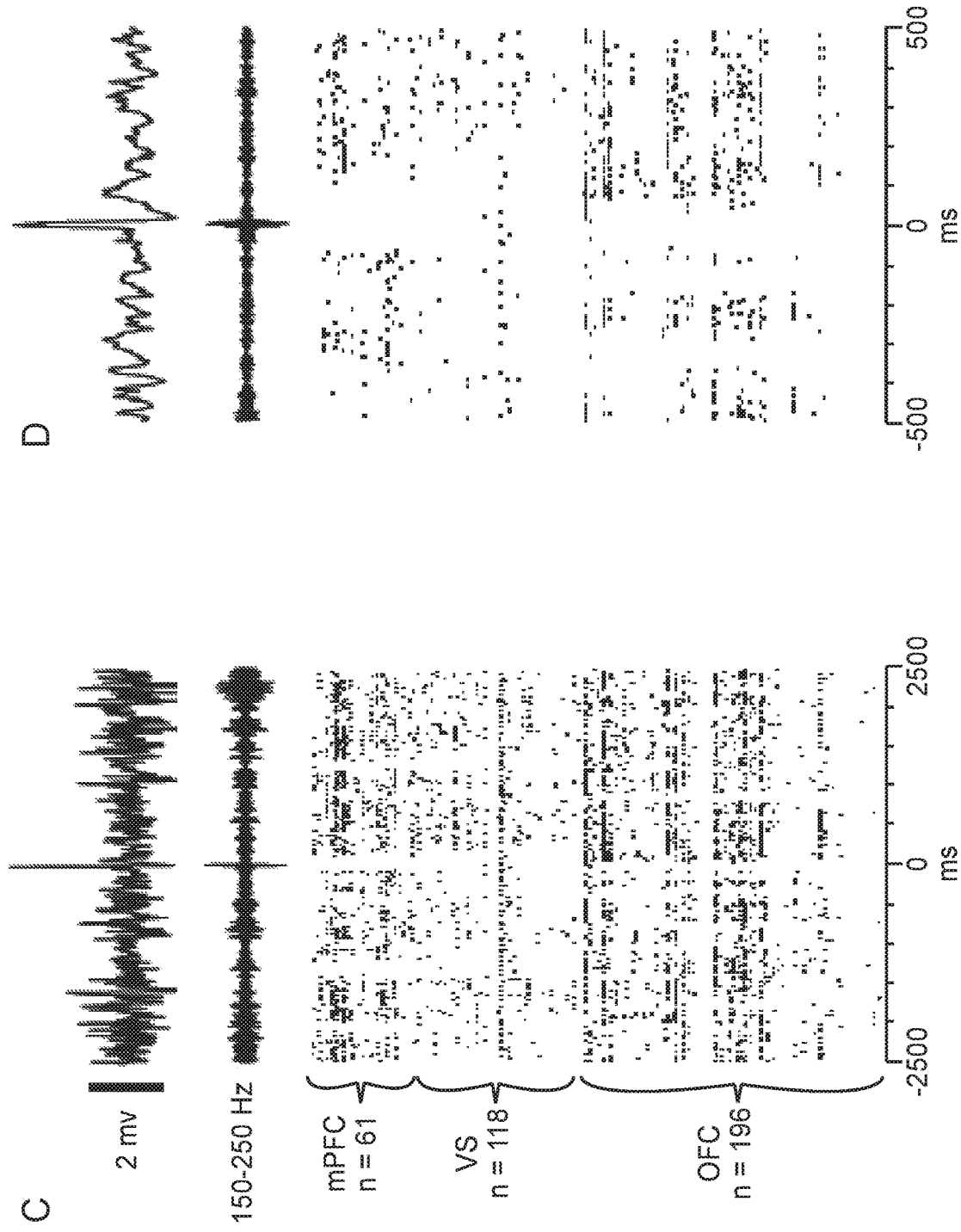

A

B

C

D

A

B

E

METHODS OF IMPLANTING A DEVICE INTO A BRAIN

CROSS-REFERENCE

This application claims the benefit of U.S. Provisional Patent Application No. 62/581,437, filed Nov. 3, 2017, which application is incorporated herein by reference in its entirety.

STATEMENT REGARDING FEDERALLY SPONSORED RESEARCH

This invention was made with government support under Grant No. U01 NS090537 awarded by the National Institutes of Health. The government has certain rights in the invention.

INTRODUCTION

The brain is a massively interconnected neuronal network organized into specialized circuits. Even primary sensory areas, once thought to support relatively simple information extraction, are now known to be parts of complex feedback circuits spanning large ensembles of neurons distributed across anatomically and/or functionally connected regions. While the functions of these circuits depend upon millisecond timescale interactions, the structure of the underlying networks is remodeled on timescales of months.

However, current approaches lack the combination of resolution, spatial coverage, longevity, and stability to measure and understand the detailed dynamics across these neuronal networks. For example, one approach to chronic implantation for multiple penetrating devices involves a skull-fixed implant, wherein the array is directly tethered to the skull. Over time, the rigid electrodes shear the softer neural tissue, and the neural signal decays. New methods of implanting devices into a brain to provide direct access to the brain with a low risk of complication and permit large-scale recordings of brain activity are needed to address serious drawbacks.

The methods, devices, and systems disclosed herein address the above limitations and fulfill other needs.

SUMMARY

The present disclosure generally provides methods of implanting an implantable device in contact with a brain of a subject. Also provided are kits and systems for the implantation of one or more implantable devices.

Provided herein is a method of implanting an implantable device in contact with a brain of a subject, the method including: a) removing a portion of a skull and a portion of an underlying dura of a subject to create an opening in the skull to expose a surface of the brain of the subject; b) positioning the implantable device in contact with the brain of the subject, wherein the implantable device includes a plurality of electrodes and a measuring device; c) positioning a first polymeric material in contact with the surface of the brain to form a seal; d) positioning a second polymeric material on the first polymeric material, wherein the second polymeric material has a higher viscosity than the first polymeric material; and e) positioning a capping element over the opening in the skull.

In some embodiments, the positioning of the implantable device in contact with the brain is on the surface of the brain. In some embodiments, the positioning of the implantable device in contact with the brain is within the brain under the surface.

In some embodiments, the first polymeric material includes a biocompatible material. In some embodiments, the second polymeric material includes a biocompatible material. In some embodiments, the biocompatible material includes a silicone elastomer. In some embodiments, the second polymeric material includes a harder material than the first polymeric material.

In some embodiments, the positioning the first polymeric material further includes providing strain relief for the positioning of the implantable device in contact with the brain of the subject. In some embodiments, the positioning of the first polymeric material includes applying a pressure to the implantable device that matches intracranial pressure. In some embodiments, the pressure applied by the first polymeric material is a downward pressure. In some embodiments, the positioning of the second polymeric material includes applying a pressure to the implantable device that matches intracranial pressure. In some embodiments, the pressure applied by the second polymeric material is a downward pressure.

In some embodiments the capping element includes at least two materials, wherein the at least two material includes a casing and a hard outer layer. In some embodiments, the casing is a 3D-printed material. In some embodiments, the hard outer layer includes a titanium plate. In some embodiments, the titanium plate is anchored to the skull.

In some embodiments, the method further includes positioning an implantation device around the opening in the skull, wherein the implantation device includes a lumen and walls, wherein the lumen provides access to the surface of the brain. In some embodiments, the implantation device is placed orthogonal to the surface of the skull. In some embodiments, the walls of the implantation device include a bottom surface, wherein the bottom surface conforms to a perimeter contour of the surface of the skull. In some embodiments, the implantation device includes a 3D-printed material. In some embodiments, the implantation device includes a biocompatible material, wherein the biocompatible material is silicon. In some embodiments, the implantation device further includes: a first polymeric material within the lumen; and a second polymeric material positioned on the first polymeric material, wherein the second polymeric material has a higher viscosity than the first polymeric material.

Also provided herein is a system for implanting an implantable device, the system including: a) one or more implantable devices; b) an implantation device; c) a first polymeric material; d) a second polymeric material, wherein the second polymeric material has a higher viscosity than the first polymeric material; and e) a capping element. In some embodiments, provided herein is a system for implanting an implantable device, the system including: a) one or more implantable devices; b) a first polymeric material; c) a second polymeric material, wherein the second polymeric material has a higher viscosity than the first polymeric material; and d) a capping element. In other embodiments, a system provided herein is for implanting an implantable device, the system including: a) one or more implantable devices; b) a first polymeric material; and c) a second polymeric material, wherein the second polymeric material has a higher viscosity than the first polymeric material.

BRIEF DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present invention.

DEFINITIONS

Figure 1:
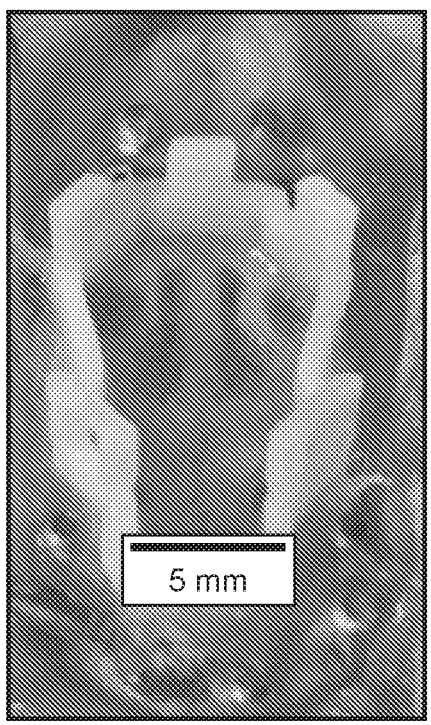
FIG. 1, Panels A-H depict the surgical approach and implant construction described herein, with a silicone elastomer fill to protect soft passive electrical components, moisture-sensitive active electrical components, and strain relief for their soft-hard interface.
Figure 1:
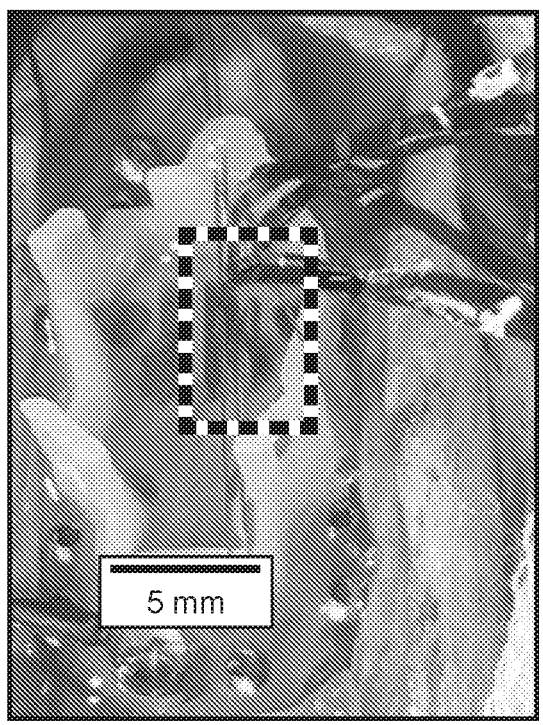
Figure 1:
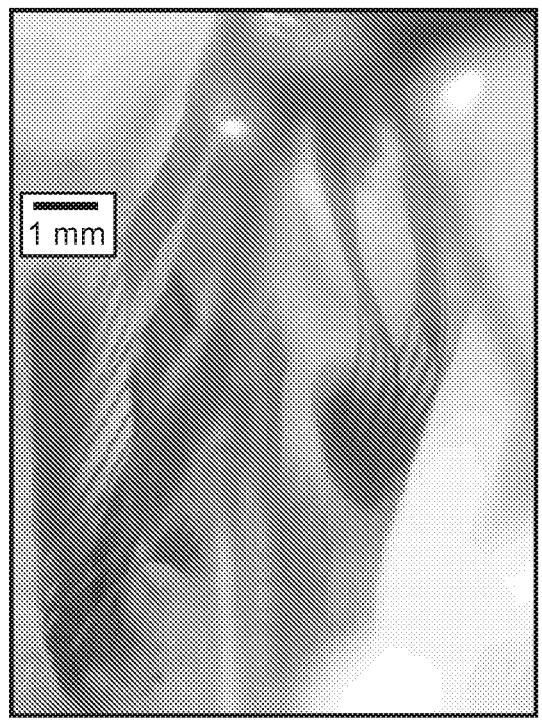
Figure 1:
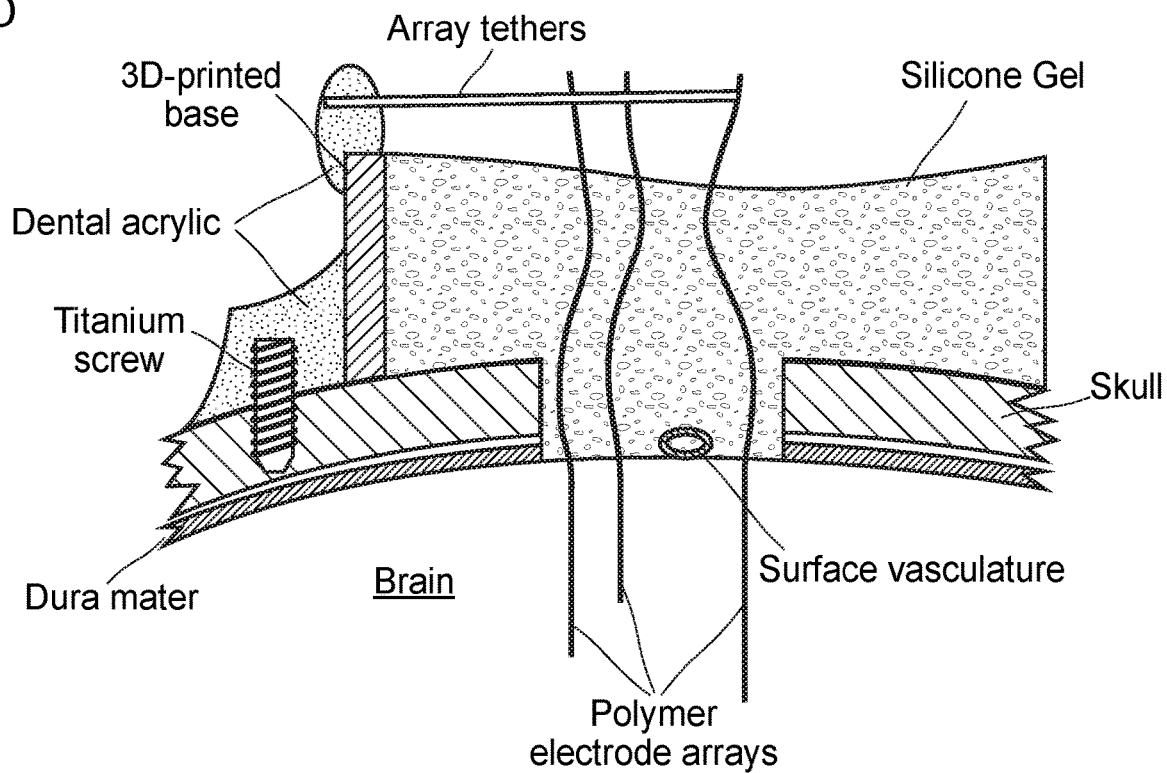
Figure 1:
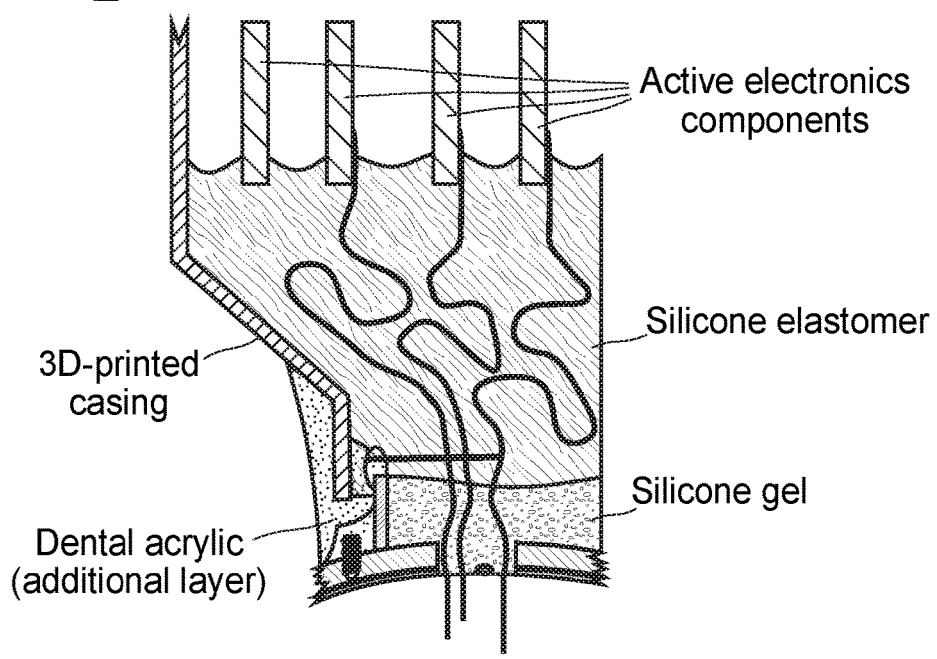
Figure 1:
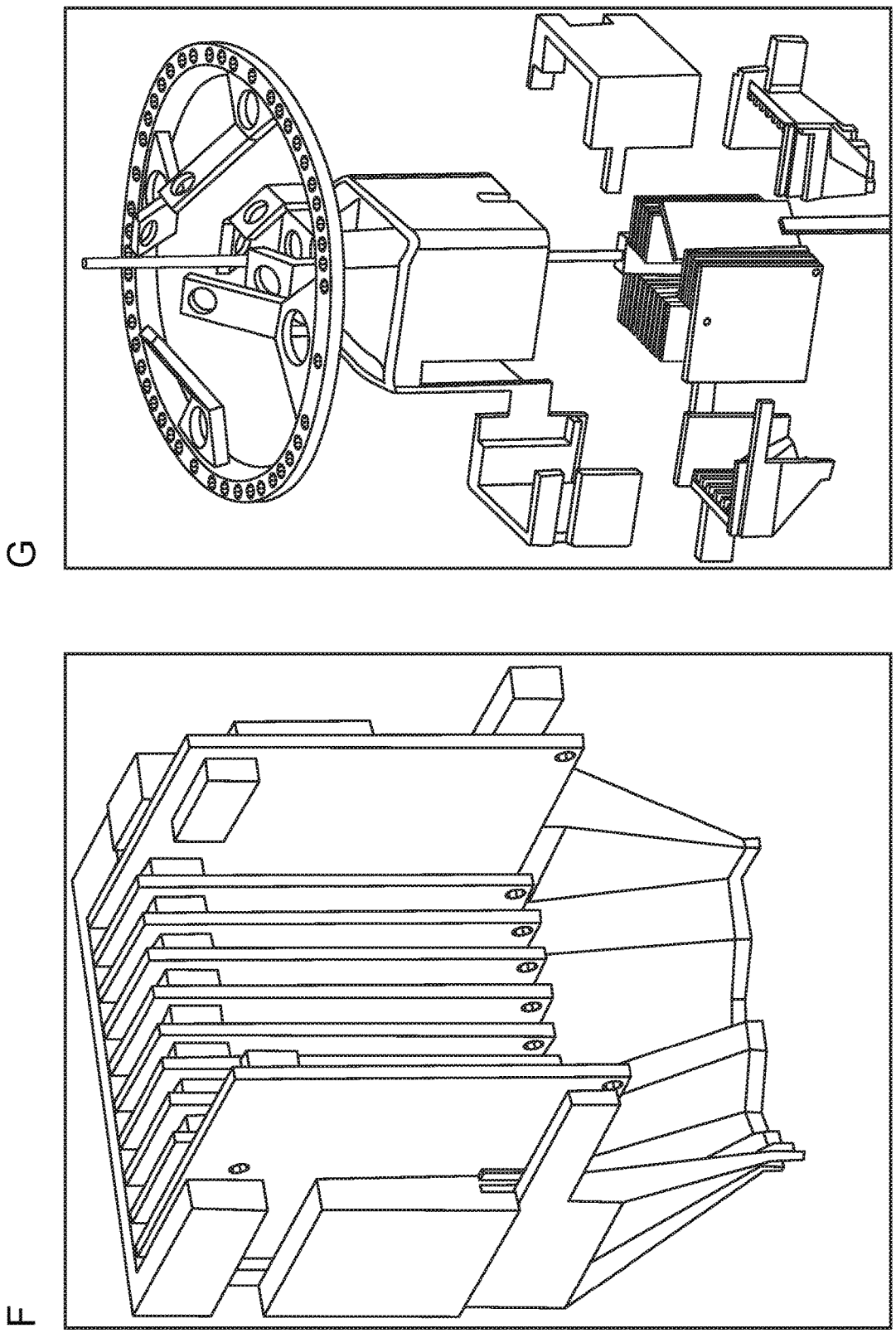
Figure 1:

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e g a non-human primate, a murine (e.g., a mouse, a rat), lagomorpha, etc. may be used for experimental investigations.

The term "biocompatible," as used herein, refers to a property of a material that allows for prolonged contact with a tissue in a subject without causing toxicity or significant damage.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "target," as used in reference to a tissue or site, refers to a tissue or location within a subject's body to which an active agent is, or is intended to be, delivered by an implant of the present disclosure. The target tissue can include pathological tissue, e.g., cancerous tissue, that is to be treated by the active agent, or can include tissue where occurrence or recurrence of pathology, e.g., cancer, is to be prevented or delayed. A "non-target tissue" may refer to any tissue that is not the intended target for delivering an active agent using the implant. In some cases, the non-target tissue is a tissue that is adjacent the target tissue. In some cases, the non-target tissue includes a systemically circulating tissue, such as blood.

As used herein, the term "copolymer" describes a polymer which contains more than one type of subunit. The term encompasses polymer which include two, three, four, five, or six types of subunits.

The term "curing" as used herein, is intended to refer to any material that can be stably stored for an extended period of time in a first, malleable or flexible form without loss of flexibility, and be transformed to a second, hardened form after application of an initiating energy thereto. No specific mechanism of hardening is preferred, and it should be understood that any mode of shape memory material transformation is contemplated herein.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an implantable device" includes a plurality of such implantable devices and reference to "the implantation device" includes reference to one or more implantation devices and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure generally provides methods of implanting an implantable device in contact with a brain of a subject. Also provided are kits and systems for the implantation of one or more implantable devices.

Provided herein is a largescale, multisite recording platform that integrates biocompatible polymer electrodes with a modular stacking headstage design which supports, e.g., 1024 channels, of recording. The methods provide a large surface-area access to brain tissue while still providing enough volume and heat dissipation for a plurality of electrodes and associated components. Also provided herein are methods to allow for one or more implantation devices to be implanted in contact with the brain in the absence of a dural closure or duraplasty around each penetration or implantation device.

Methods
Method of Implanting an Implantable Device in Contact with a Brain

Provided herein is a method of implanting an implantable device in contact with a brain of a subject, including: a) removing a portion of a skull and a portion of an underlying dura of a subject to create an opening in the skull to expose a surface of the brain of the subject; b) positioning the implantable device in contact with the brain of the subject, wherein the implantable device includes a plurality of electrodes and a measuring device; c) positioning a first polymeric material in contact with the surface of the brain to form a seal; d) positioning a second polymeric material on the first polymeric material, wherein the second polymeric material has a higher viscosity than the first polymeric material; and e) positioning a capping element over the opening in the skull.

Positioning the Implantable Device in Contact with the Brain

The present disclosure generally provides methods for positioning an implantable device in contact with the brain.

In some embodiments, the step of removing a portion of a skull and a portion of an underlying dura of a subject may be carried out by any method known in the art. For example, a portion of a skull and a portion of an underlying dura of a subject may be removed by performing a craniectomy and a durectomy, including but not limited to, performing skull base surgeries, decompressive craniectomies, suboccipital craniectomies, and the like. In some embodiments, a surgical opening exposes a surface of the brain of the subject, including exposure to one or more areas in the brain, such as, for example, around the medial prefrontal cortex (mPFC, including prelimbic and anterior cingulate cortices), ventral striatum (VS, primarily nucleus accumbens shell), orbitofrontal cortex (OFC, primarily lateral orbitofrontal cortex), and dorsal hippocampus (dHPC).

In some embodiments, the positioning of the implantable device in contact with the brain of the subject is followed by positioning a first polymeric material in contact with the surface of the brain to form a seal; positioning a second polymeric material on the first polymeric material, wherein the second polymeric material has a higher viscosity than the first polymeric material; and positioning a capping element over the opening in the skull. An embodiment of the implantable device for implanting in contact with the brain includes a plurality of electrodes and a measuring device.

In some embodiments, the positioning the implantable device in contact with the brain of the subject further includes adhering the plurality of electrodes to a removable stiffener to facilitate the positioning of the implantable device.

Implantable Device

The methods provided herein generally involve an implantable device positioned in contact with the brain of a subject, wherein the implantable device includes a plurality if electrodes and a measuring device.

In some embodiments, the plurality of electrodes are partially or substantially embedded into the second polymeric material. In some embodiments, the plurality of electrodes and the measuring device are fully embedded into the second polymeric material. In some embodiments, only a portion of the measuring device is embedded into the second polymeric material.

In some embodiments, the plurality of electrodes include a flexible polyimide material. The polyimide material can be any biocompatible material that is suitable for use in the present methods. The implantation device can have any physical and material properties (e.g., inner diameter, wall thickness, flexibility, tensile strength, etc.) suitable for use in the present methods. The physical and material properties can in some cases be substantially uniform along the length of the device that is in contact with a brain so as to provide controlled delivery. In some embodiments, the plurality of electrodes include one or more platinum electrodes extending across a length of the implantable device.

The implantable device can have any dimensions suitable for positioning in contact with the brain of the subject. The inner diameter of the implantable device may be 0.1 mm or more, e.g., 0.3 mm or more, 0.5 mm or more, including 0.6 mm or more, and may be 5.0 mm or less, e.g., 3.0 mm or less, 1.0 mm or less, including 0.9 mm or less. In some cases, the inner diameter of the implantable device is in the range of 0.1 to 5.0 mm, e.g., 0.1 to 3.0 mm, 0.3 to 1.0 mm, including 0.5 to 0.9 mm. The outer diameter of the implantable device may be 0.5 mm or more, e.g., 0.8 mm or more, 1.0 mm or more, including 1.2 mm or more, and may be 10 mm or less, e.g., 5.0 mm or less, 3.0 mm or less, including 2.0 mm or less. In some cases, the inner diameter of the implantable device is in the range of 0.5 to 10 mm, e.g., 0.8 to 5.0 mm, 1.0 to 3.0 mm, including 1.2 to 2.0 mm. The wall thickness of the implantable device may be 0.1 mm or more, e.g., 0.2 mm or more, 0.3 mm or more, including 0.4 mm or more, and may be 3.0 mm or less, e.g., 1.0 mm or less, 0.8 mm or less, including 0.6 mm or less. In some cases, the wall thickness of the implantable device is in the range of 0.1 to 3.0 mm, e g, 0.1 to 1.0 mm, 0.2 to 0.8 mm, including 0.3 to 0.6 mm.

In some embodiments, the plurality of electrodes include 64 channels or 1024 channels. In some embodiments, the implantation device includes one or more shanks, e.g., one shank, two shanks, three shanks, or four shanks. In some embodiments, each shank includes from about 16-channels to about 64-channels per shank, e.g., 18-channels, 24-channels, 32-channels, 36-channels, 48-channels, or 64-channels. In some embodiments, the inter-shank spacing, e.g., the spacing distance between each shank, is about 0.25 mm. The inter-shank spacing between each shank may be about 0.1 mm to about 30.0 mm, e.g., 1.5 mm, 3.0 mm, 6.0 mm, 9.0 mm, 12.0 mm, 15.0 mm, 20.0 mm, 30.0 mm, or any distance between shanks so as to avoid recording the same neurons on more than one electrode array.

In some embodiments, the implantation device includes two shanks, 18-channels per shank. In some embodiments, the implantation device is a two-shank, 36-electrode, polymer array. The electrodes are divided evenly between the two shanks. The shanks are both 6 mm long and 100 μm wide and are separated by 2 mm Each electrode is 20 μm in diameter with a center-to-center spacing of 110 μm. On each shank, the electrodes are arranged in a single-line on the outside edge of the device. The electrodes are placed off-center so they are located closer to the non-damaged tissue. The electrode distribution was specially designed to record local field potentials.

In some embodiments, the measuring device includes a communication unit. In some embodiments, the communication unit is a wireless communication unit. In some embodiments, the wireless communication unit includes Radio-frequency Identification (RFID), Bluetooth, or Near Field Communication (NFC).

In some embodiments, the positioning the implantable device in contact with the brain of the subject further includes anchoring the measuring device to the surface of the brain. In some embodiments, the anchoring includes affixing the measuring device with a biocompatible material. In some embodiments, the biocompatible material includes a polyimide tether. The implantable device can include any suitable element for securing the implantable device to tissue at the site of implantation. In some cases, the implant includes one or more suture tabs. Any suitable suture tab may be used. In some embodiments, the implantable device includes one or more polyimide tethers that may be used to secure the implant at the site of implantation. In some cases, one or more polyimide tethers may be affixed to the implantable devices for use in securing the implantable device at the site of implantation.

A variety of polymers from synthetic and/or natural sources can be used for the positioning of the implantable devices in contact with the brain of a subject, in addition to composing the implantable device. The biocompatible material can be made from a homopolymer, a copolymer, or blended polymers; the homopolymer, copolymer, or blended polymer can be degradable or non-degradable. For example, lactic or polylactic acid or glycolic or polyglycolic acid can be utilized to form poly(lactide) (PLA) or poly(L-lactide) (PLLA) nanofibers or poly(glycolide) (PGA) nanofibers. Biocompatible material scan also be made from more than one monomer or subunit thus forming a co-polymer, ter-polymer, etc. For example, lactic or polylactic acid and be combined with glycolic acid or polyglycolic acid to form the copolymer poly(lactide-co-glycolide) (PLGA). Other copolymers may include poly(ethyleneco-vinyl) alcohol). In an exemplary embodiment, a biocompatible material includes a polymer or subunit which is a member selected from an aliphatic polyester, a polyalkylene oxide, polydimethylsiloxane, polyurethane, expanded polytetrafluoroethylene (ePTFE), polyvinylalcohol, polylysine, collagen, laminin, fibronectin, elastin, alginate, fibrin, hyaluronic acid, proteoglycans, polypeptides and combinations thereof. In another exemplary embodiment, a biocompatible material includes two different polymers or subunits which are members selected from an aliphatic polyester, a polyalkylene oxide, polydimethylsiloxane, polyurethane, ePTFE, polyvinylalcohol, polylysine, collagen, laminin, fibronectin, elastin, alginate, fibrin, hyaluronic acid, proteoglycans, polypeptides and combinations thereof. In another exemplary embodiment, a biocompatible material includes three different polymers or subunits which are members selected from an aliphatic polyester, a polyalkylene oxide, polydimethylsiloxane, polyurethane, ePTFE, polyvinylalcohol, polylysine, collagen, laminin, fibronectin, elastin, alginate, fibrin, hyaluronic acid, proteoglycans, polypeptides and combinations thereof. In an exemplary embodiment, the aliphatic polyester is linear or branched. In another exemplary embodiment, the linear aliphatic polyester is a member selected from lactic acid (D- or L-), lactide, poly(lactic acid), poly(lactide) glycolic acid, poly(glycolic acid), poly(glycolide), glycolide, poly(lactideco-glycolide), poly(lactic acid-co-glycolic acid), polycaprolactone and combinations thereof. In another exemplary embodiment, the aliphatic polyester may be branched and may include at least one member selected from lactic acid (D- or L-), lactide, poly (lactic acid), poly(lactide) glycolic acid, poly(glycolic acid), poly(glycolide), glycolide, poly(lactideco-glycolide), poly (lactic acid-co-glycolic acid), polycaprolactone and combinations thereof which is conjugated to a linker or a biomolecule. In an exemplary embodiment, a polymer may be a polyalkylene oxide selected from polyethylene oxide, polyethylene glycol, polypropylene oxide, polypropylene glycol and combinations thereof.

Removable Stiffener

The methods provided herein may additionally involve a removable stiffener to facilitate the implanting of an implantable device in contact with a brain of a subject. In some embodiments, the removable stiffener includes a biocompatible material. Examples of biocompatible material suitable for the methods provided herein include, but are not limited to, those described above. In some embodiments, the biocompatible material includes silicon. In some embodiments, the adhering includes disposing an adhesive on a top surface of the plurality of electrodes. In some embodiments, the adhesive includes polyethylene glycol. Other examples of suitable adhesives include, but are not limited to, natural adhesives, semisynthetic adhesives, and synthetic adhesives, such as resin, silicone, silastic medical adhesive type A, and Sofreliner primer.

Positioning the First and Second Polymeric Material

The present disclosure generally provides methods for positioning a first polymeric material in contact with the surface of the brain to form a seal, followed by the positioning of a second polymeric material on the first polymeric material, wherein the second polymeric material has a higher viscosity than the first polymeric material.

In some embodiments, the first polymeric material forms a seal around the brain and intracranial space while still allowing for biocompatibility with neural tissue, strain relief for implantable devices in contact with the brain of a subject, including on the surface of the brain and under the surface of the brain, and a way for the implantable devices to pass through the seal. In some embodiments, the first polymeric material covers the edges of a durectomy. In some embodiments, the first polymeric material positioned in contact with the surface of the brain to form a seal includes a low-viscosity silicon elastomer, applied directly onto the brain. In some embodiments, the first polymeric material is a biocompatible material. In some embodiments, the first polymeric material is soft and not sticky. In some embodiments, the biocompatible material is DOW 3-4680.

In some embodiments, a downward force must be applied to the surgical opening after positioning the first polymeric material in contact with the brain of the subject and/or positioning the second polymeric material on the first polymeric material, allowing pressure at the opening to match that of intracranial pressure. In some embodiments, the downward pressure may be from about 5.0 mmHg to about 20.0 mmHg, e.g., 7.0 mmHg, 10.0 mmHg, 12.0 mmHg, 15.0 mmHg, 18.0 mmHg, or 20.0 mmHg. In some cases, the downward pressure reduces the risk of herniation and dampens brain pulsations and impact. In some cases, the hard-soft interface where the implantable devices meet the plurality of electrodes are positioned in a manner suitable for the methods provided herein, such that any force applied distributes along the length of the implantable device and does not concentrate specifically at the hard-soft interface. In some embodiments, the plurality of electrodes undergo further decoupling from impact and associated movement, such as by adding a shock-absorbent material such as silicone, foam, or rubber, or adding a protective shell.

In some embodiments, the first polymeric material facilitates the application of a pressure. In some embodiments, the second polymeric material facilitates the application of a pressure. In some embodiments, the pressure applied is a downward pressure. In some embodiments, the application of pressure may be due to an additional component, such as a membrane, a film or a flexible sheet.

In some embodiments, the second polymeric material is positioned on the first polymeric material, wherein the second polymeric material has a higher viscosity than the first polymeric material. Using the methods disclosed herein, the viscosity of the second polymeric material may differ from that of the first polymeric material, e.g., at least 2 fold, at least 3 fold, at least 5 fold, at least 10 fold, at least 20 fold, at least 30 fold, at least 40 fold, at least 50 fold, at least 100 fold, or more. In some embodiments, the second polymeric material is a biocompatible material. In some embodiments, the second polymeric material is Quick-Sil®.

In some embodiments, the plurality of electrodes pass through the second polymeric material. In some embodiments, the plurality of electrodes substantially pass through the first and/or second polymeric material, such that, e.g., at least 1%, at least 3%, at least 5%, at least 8%, at least 10%, at least 30%, at least 50%, at least 75%, at least 100% of the length of the implantable device including the plurality of electrodes and the measuring device is embedded in the second polymeric material.

In some embodiments, multiple layers of a polymeric material may be positioned on the surface of the brain, e.g., one or more, two or more, three or more, four or more, or five or more. In some embodiments, the multiple layers of polymeric material include at least one lower-viscosity material and at least one higher-viscosity material, relative to each other, wherein the higher-viscosity material is positioned on top of the lower-viscosity material. In some embodiments, the multiple layers of polymeric material include multiple layers of a higher-viscosity material.

The polymeric materials of the present disclosure can be produced in a variety of ways. In an exemplary embodiment, the polymeric material can be produced by electrospinning. Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e., small diameter, fibers. The resulting films (or membranes) from these small diameter fibers have very large surface area to volume ratios and small pore sizes. A detailed description of electrospinning apparatus is provided in Zong, et al., Polymer, 43(16):4403-4412 (2002); Rosen et al., Ann Plast Surg., 25:375-87 (1990) Kim, K., Biomaterials 2003, 24, (27), 4977-85; Zong, X., Biomaterials 2005, 26, (26), 5330-8. After electrospinninng, extrusion and molding can be utilized to further fashion the polymeric material.

The polymer solution can be produced by dissolving the polymer in appropriate solvents. The polymer solution can be subsequently loaded into a syringe assembly. The polymer used to form the polymeric material is first dissolved in a solvent. The solvent can be any solvent which is capable of dissolving the polymer monomers and/or subunits and providing a polymer solution capable of conducting and being electrospun. Typical solvents include a solvent selected from N,N-Dimethyl formamide (DMF), tetrahydrofuran (THF), methylene chloride, dioxane, ethanol, hexafluoroisopropanol (HFIP), chloroform, water and combinations thereof. The polymer solution can optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$ or mixtures of these salts.

In some embodiments, a variety of hardening mechanisms can be utilized, depending upon material selection, including, for example, curing that is initiated by ultraviolet radiation, visible light, blue light, infrared radiation, radio frequency radiation, x-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation, and the like.

Activatable polymeric materials include thioisocyanates, aldehydes, isocyanates, divinyl compounds, epoxides or acrylates. In addition, photoactivatable crosslinkable groups such as succinimidyl azido salicylate, succinimidyl-azidobenzoate, succinimidyl dithio acetate, azidoiodobenzene, fluoro nitrophenylazide, salicylate azides, benzophenonemaleimide, and the like may be used as photoactivatable crosslinking reagents. The material may also consist of a thin coating, e.g. overlying a shape memory alloy, which can be activated by external forces such as laser, radio frequency, ultrasound or the like, with the same hardening result taking place.

Biocompatible Material

The methods provided herein generally involve the use of a biocompatible material. Some relevant factors to be considered in choosing a polymeric material for the first and second polymeric material include: compatibility of the polymer with the biological environment of the implantable device, compatibility of the subject with the polymer, ease of manufacture, a half-life in the physiological environment, etc. Depending on the relative importance of these characteristics, the compositions can be varied. Several such polymers and their methods of preparation are well-known in the art. See, for example, U.S. Pat. Nos. 4,304,765;

4,668,506; 4,959,217; 4,144,317, and 5,824,074, Encyclopedia of Polymer Science and Technology, Vol. 3, published by Interscience Publishers, Inc., New York, latest edition, and Handbook of Common Polymers by Scott, J. R. and Roff, W. J., published by CRC Press, Cleveland, Ohio, latest edition, the disclosures of which are incorporated herein by reference.

Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly (methacrylic acid)-t butyl ester, polytetrafluoroethylene, polyperfluoropropylene, poly N-vinyl carbazole, poly(m-ethyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(lactide-co-glycolide); poly(hydroxybutyrate); poly(hydroxybutyrate-co-valerate); polydioxanone; polyorthoester; polyanhydride; poly(glycolic acid) (PGA); poly (D,L-lactide) (PDLL); poly(L-Lactide)(PLL); copolymers of PGA, PDLA, and/or PLA; poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Other polymers of interest may be homopolymers, copolymers, straight, branched-chain, or cross-linked derivatives. Suitable polymers include: polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3Dimethyl butanoate copolymer, and ethylene-vinyl benzoate copolymer, or mixtures thereof.

Implantation Device

In some embodiments, the method further includes positioning an implantation device around the opening in the skull. In some embodiments, the implantation device includes a lumen and walls, wherein the lumen provides access to the surface of the brain. In some embodiments, the implantation device is placed orthogonal to the surface of the skull. In some embodiments, the walls of the implantation device include a bottom surface, wherein the bottom surface conforms to a perimeter contour of the surface of the skull. In some embodiments, the walls of the implantation device include a shaped cross-section, for example, but not limited to, frustoconical shaped, cylindrical shaped, circular shaped, and rectangular shaped cross sections. In some embodiments, the implantation device includes a 3D-printed material. In some embodiments, the 3D-material includes a biocompatible material, wherein the biocompatible material is silicon. In some embodiments, the implantation device further includes: a first polymeric material within the lumen; and a second polymeric material positioned on the first polymeric material, wherein the second polymeric material has a higher viscosity than the first polymeric material. Examples of biocompatible materials include, but are not limited to, those described above for implantable devices as provided herein.

In some embodiments, the positioning of an implantation device further includes anchoring the implantation device to the skull. In some embodiments, the anchoring includes screwing the implantation device with one or more screws. In some embodiments, the screws include titanium. In some embodiments, the anchoring includes adhering the implantation device to a surface of the skull using an adhesive disposed on a bottom surface of the walls of the implantation device in contact with the surface of the skull. In some embodiments, the adhesive is methylmethacrylate with 4-methacryloyloxyethy trimellitate anhydride (MMA with 4-META). Other examples of suitable adhesives are known in the art. Additional polymer may be added to secure the implantation device. In some embodiments, the method further includes removing the implantation device from the opening in the skull.

Positioning a Capping Element Over the Opening in the Skull

The present disclosure generally provides methods for positioning a capping element over the opening in the skull. The capping element facilitates the encasing of the plurality of electrodes. In some embodiments, the encasing includes a 3D printed casing. In some embodiments the 3D printed casing includes a biocompatible material.

In some embodiments, an outer layer is positioned on top of the encasing. In some embodiments, the outer layer is a harder material than the encasing material. In some embodiments, the outer layer is affixed to the inner implantable device via a shock-dampening material to guard against impact damage. In some embodiments, the shock-dampening material is a biocompatible material. In some embodiments, the outer layer can be anchored to the skull of the subject. The assembly allows for the dura and skull to be left disrupted while still preventing brain herniation and cerebrospinal fluid leakage, reduction of infection risk, correction of intracranial pressure around the implant site, and dampening of brain pulsations and impact. In some embodiments, further strain relief is provided by adding additional layers. In some embodiments, additional layers of increasingly rigid silicone elastomer can be added to provide more graded strain relief and eventual protection of the hard-soft interface from bending fatigue.

Utility

The methods disclosed herein find use in any in vitro or in vivo application in which it is desirable to implant an implantable device in contact with a brain of a subject. In some cases, the methods may be conducted multiple times. In some cases, the methods provide a long-lasting effect especially if the implantable devices become integrated into the brain.

For example, the subject methods may be used to collect data from different regions of a distributed neural circuit simultaneously, with minimal or no experiment-specific implantation components. The methods provided herein require that recording sites be flexibly distributed across the brain, yet in high enough density to yield appreciable numbers of single neurons from each region of interest. The methods allow for high-resolution sample in each targeted region. Without intending to be bound by any particular theory, this requires a tradeoff between one or more, e.g. two or more, three or more, four or more, large, high-density arrays with rigid geometries, and many lower-density arrays (or single channels) able to be arbitrarily and precisely distributed across the brain.

The subject methods find use in providing recordings for long periods of time, from about 1 month to about 3 years, e.g., 1 month, 5 months, 10 months, 15 months, 20 months, 25 months, 30 months, or 35 months. The recordings are stable enough to track at least 5% of implantable devices, e.g., at least 10%, at least 20%, at least 30%, at least 40%, at least 50%, at least 60%, at least 70%, at least 80%, at least 90%, at least 95%. The implantable devices may elucidate large-scale electrophysiologic interrogation of how distributed circuits function and evolve throughout the lifetime of a subject.

The subject methods find use in providing direct, large surface area access to the brain while still providing requisite volume and heat dissipation for a plurality of electrodes in excess of 9 $cm^3$ and 1.5 Watts. In some embodiments, the surface area exposing the brain spans more than 2 $cm^3$, e.g. 3 $cm^3$ or more, 4 $cm^3$ or more, 5 $cm^3$ or more, 6 $cm^3$ or more, 7 $cm^3$ or more, or 8 $cm^3$ or more. Direct access to the surface of the brain in the absence of intact or synthetic dura proximal to the brain results in pulsations of the brain and herniation due to intracranial pressure, which in turn reduces stability of the penetrating implantable device. The subject methods address the above limitations in the absence of dural closure or duraplasty around each penetration of the implantable device. The methods provided herein include positioning of the first polymeric material in contact with the surface of the brain to form a seal; positioning a second polymeric material on the first polymeric material, wherein the second polymeric material has a higher viscosity than the first polymeric material; and positioning a capping element over the opening in the skull. The use of polymeric materials and the pressure applied match the intracranial pressure and prevent cerebrospinal fluid leakage, and to provide strain relief for implantable devices. In some embodiments, the remaining portions of the implantable device not in the subarachnoid space are semi-suspended in the polymeric materials and to the sides of the chamber. In some embodiments, an appropriately sized measuring device may be included in an impact-resistant environment, either affixed or semi-floating.

The subject methods find use in facilitating a higher channel count of implantable devices and permitting dense, distributed recordings from target areas separated from about 0.1 mm to about 30.0 mm. In some embodiments, a plurality of electrodes may be fully embedded within the polymeric materials. The plurality of electrodes may range in size from about 0.1 mm to about 1.3 mm, e.g., about 0.5 mm, about 0.8 mm, about 1.0 mm, about 1.2 mm, or about 1.3 mm.

The subject methods may be applied to any disease, disorder, or natural cellular process that would benefit from implanting an implantable device in contact with the brain. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

For example, the subject methods find use in treating genetic disorders. Any genetic disorder may be treated by the subject compositions and methods, including, for example, muscular dystrophies, e.g., Duchenne muscular dystrophy, limb girdle muscular dystrophy A, B, C, D; muscular conditions, e.g., sarcopenia, muscle injury, and cachexia; and neurodegenerative diseases, e.g., Parkinson's' disease, hemophilia, adenosine deaminase deficiency, sickle cell disease, X-Linked Severe Combined Immunodeficiency (SCID-X1), thalassemia, cystic fibrosis, alpha-1 anti-trypsin deficiency, diamond-blackfan anemia, Gaucher's disease, growth hormone deficiency, and the like.

As one non-limiting example, the subject methods may be used to treat nervous system conditions and to protect the CNS against nervous system conditions, e.g. neurodegenerative diseases, including, for example, e.g. Parkinson's Disease, Alzheimer's Disease, Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression), childhood disorders (e.g. attention deficit disorder, autistic disorders), cognitive disorders (e.g. delirium, dementia), schizophrenia, substance related disorders (e.g. addiction), eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, traumatic brain injury, and spinal cord injury.

In some embodiments, the subject methods find use in treating a psychiatric disorder or condition or symptoms where excessive apprehension, uneasiness or fear causes psychological distress or dissociative reaction and includes generalized anxiety disorder, insomnia, depression, pain disorder, phobia (including specific phobias such as social phobia and agoraphobia, panic disorder, Obsessive-Compulsive Disorder, Post traumatic stress disorder (PTSD) and the like.

Other examples of how the subject methods may be used to treat medical conditions are disclosed elsewhere herein, or would be readily apparent to the ordinarily skilled artisan.

Systems

The present disclosure provides a system including: a) one or more implantable devices; b) an implantation device; c) a first polymeric material; d) a second polymeric material, wherein the second polymeric material has a higher viscosity than the first polymeric material; and e) a capping element. In some embodiments, the system includes: a) one or more implantable devices; b) a first polymeric material; c) a second polymeric material, wherein the second polymeric material has a higher viscosity than the first polymeric material; and d) a capping element. In other embodiments, a system includes: a) one or more implantable devices; b) a first polymeric material; and c) a second polymeric material, wherein the second polymeric material has a higher viscosity than the first polymeric material.

In some embodiments, the system can further include one or more additional elements, such as a one or more polymeric materials, e.g. a third polymeric material or a fourth polymeric material. In some embodiments, the systems may include a biocompatible material or adhesives. In some embodiments, the systems provided herein include one or more implantable devices in contact with the brain of a subject, e.g., 2 or more, 5 or more, 10 or more, 20 or more, 40 or more, 60 or more, 80 or more, or 100 or more implantable devices.

Kits

The present disclosure provides kits for carrying out a subject method. A subject kit can include one or more of (e.g., two or more, three or more, four or more, or all five): an implantable device; a first polymeric material; a second polymeric material, wherein the second polymeric material has a higher viscosity than the first polymeric material; an implantable device; and a capping element, all of which are described in detail above. The kit may also include a packaging that includes a compartment, e.g., a sterile compartment, for holding the implantable device. The packaging may be any suitable packaging for holding the implantable device. Examples of implantable device packaging and methods of packaging an implant are described in, e.g., U.S. Pat. Nos. 3,755,042, 4,482,053, 4,750,619; U.S. App. Pub. Nos. 20050268573, 20100133133, disclosures of which are incorporated herein by reference. Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Rat

All experiments were conducted in accordance with University of California San Francisco Institutional Animal Care and Use Committee and US National Institutes of Health guidelines. Rat datasets were collected from male long-evans rats (RRID: RGD_2308852), 6-23 months of age, with weights ranging from 500-600 g. All rats were fed standard rat chow (LabDiet 5001) in addition to sweetened evaporated milk for reward during behavioral performance. Rats were ordered from Charles River Laboratories at weights of 300-400 g and 3-4 months of age.

Surgical Implantation

Male long-evans rats (RRID: RGD_2308852), were implanted with polymer probe(s) at 6-12 months of age. Polymer arrays were targeted to a variety of targets (all coordinates given in millimeters relative to bregma: medial prefrontal cortex (mPFC, including prelimbic and anterior cingulate cortices; ±1.2 ML, +1.5 to +4.5 AP, −2.0 to −4.0 DV, arrays implanted 6-8° traverse from the sagittal plane, perpendicular to coronal plane), ventral striatum (VS, primarily nucleus accumbens shell; ±0.7 to +1.9 ML, +0.8 to +1.9 AP, −7.2 DV, arrays implanted parallel to midline and perpendicular to coronal), orbitofrontal cortex (OFC, primarily lateral orbitofrontal cortex; ±3.5 to 3.7 ML, +2.6 to +3.4 AP, −4.0 DV, arrays implanted at 54° sagittal from coronal plane), dorsal hippocampus (dHPC, ±2.3 to 2.8 ML, −3.5 to −4.0 AP, −4.0 to −6.0 DV, arrays implanted 45° coronal from sagittal plane). FIG. 1, Panel C depicts a view of insertion angles. For some subjects, stimulating electrodes and tetrode microdrives were also implanted at the same time, targeted to the ventral hippocampal commissure (vHC, ±1.0 ML, −1.2 or −2.0 AP) and dHPC.

Anesthesia was induced using ketamine, xylazine, atropine, and isoflurane. Every 4 hours, the animal received additional Ketamine, xylazine, and atropine.

The skull was cleaned, targets were marked, and all drilling was completed. Commercially-pure titanium (CpTi) 0-80 set screws (United Titanium, OH) were then placed around the perimeter of the implant due to its well-known ability to osseo-integrate (Le Guehennec et al., 2007). Bone dust was then cleared from the skull, and craniectomies and durectomies were completed. The skull was then briefly allowed to dry and a custom 3D-printed base piece (RGD837 Stratasys, MN) was then fixed to the skull using 4-META/MMA-TBB (Matsumura and Nakabayashi, 1988) (C&B Metabond). This base piece serves a multitude of functions including a reservoir for saline or silicone gel, an anchoring point for the polymer arrays, and a standardized interface from which the rest of the implant can be affixed and constructed during the implantation.

Polymer probes attached to silicon stiffeners using polyethylene glycol (PEG) were then inserted to the brain (Felix et al., 2013). Probe insertion involved several steps prior to the surgery, covered below in the Methods section "preparation of stiffeners and arrays for insertion." During the surgery, each of the custom 3D-printed pieces (one connected to the stiffener and polymer array, one to the stiffener only) was attached to two one-axis micromanipulators (MO-10, Narshige). In turn, the insertion device (two 3D-printed pieces and two micromanipulators) was connected to the stereotax. The array was moved to the target and adjusted to avoid surface vasculature and other arrays (1 to 15 minutes). Next, it was quickly (<5 seconds) lowered ~0.5 mm into the brain using the stereotax. A quick initial insertion was required to prevent premature softening of the PEG and detachment of stiffener and array in the cerebrospinal fluid above the brain. A micromanipulator was used to advance the stiffener and the polymer array simultaneously, until reaching the final targeted depth. The stiffener and array were lowered at a rate of ~25 μm/second until within 1 mm of the final depth, at which time the rate was reduced to ~5 μm/second (3 to 6 minutes).

Once at final depth, polymer probes were then affixed to the 3D-printed base piece using light-curable dental acrylic (Vivid Flow, Pearson Dental; 2 to 4 minutes). Next, the 3D-printed base piece was filled with saline and additional saline was dripped onto the silicon stiffener until the PEG dissolved (1 to 2 minutes). The silicon stiffener was retracted using the second micromanipulator at a rate of ~5 μm/second for the first 1 mm, and then at a rate of ~25 μm/second until the silicon stiffener was above brain surface (3 to 4 minutes). Gentle bends were allowed to form below the anchoring points on the polymer arrays, acting as strain relief. The time from mounting the insertion device to the stereotax to completion of stiffener retraction typically took 10 to 25 minutes, and largely depended on the surface vasculature and nearby arrays. Insertion was repeated for all targeted locations.

After all polymer probes were affixed, the saline filling the 3D-printed base piece was then removed and silicone gel (Dow-Corning 3-4680) was used to fill the 3D-printed base piece, providing a means to seal the durectomies and craniectomies, and also provide added support for the polymer arrays. Additional custom 3D-printed pieces were used to construct a protective case around the polymer devices and active electronic components of the implant. Silicone elastomer (Quik-sil, WPI) was then added to the remainder of the exposed polymer, with special attention to the soft polymer-rigid printed circuit board interface, and 3D-printed casing was affixed to the skull using dental acrylic.

Reagents and Data Acquisition
Polymer Arrays

The polymer arrays were fabricated at the Lawrence Livermore National Laboratory nanofabrication facility as described previously (Tooker et al., 2012b, 2012a). Briefly, devices have three trace metal layers and four polyimide layers with a total device thickness of 14 μm. All arrays had a tip angle of 45°.

Devices with an LFP configuration had 20 μm contacts in a single-line with a center-to-center distance of 100 μm, tapered shank width of 61 μm to 80 μm, 21 or 22 contacts per shank, and an edge-of-shank to edge-of-shank distance of 420 μm (center-of-shank to center-of-shank distance or pitch of 500 μm).

Figure 2:
FIG. 2, Panels A-E depict an overview of a modular 1024-channel implantation platform described herein.
Figure 2:
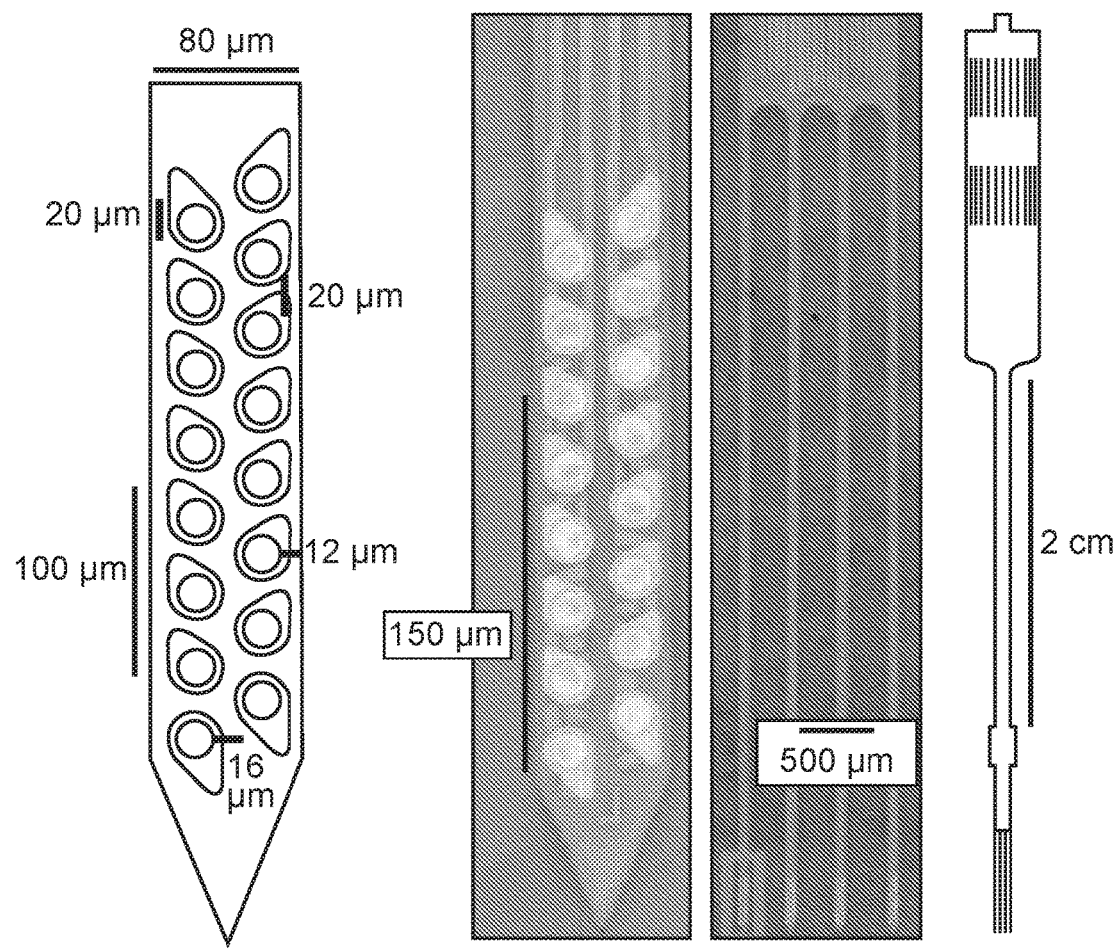
Figure 2:
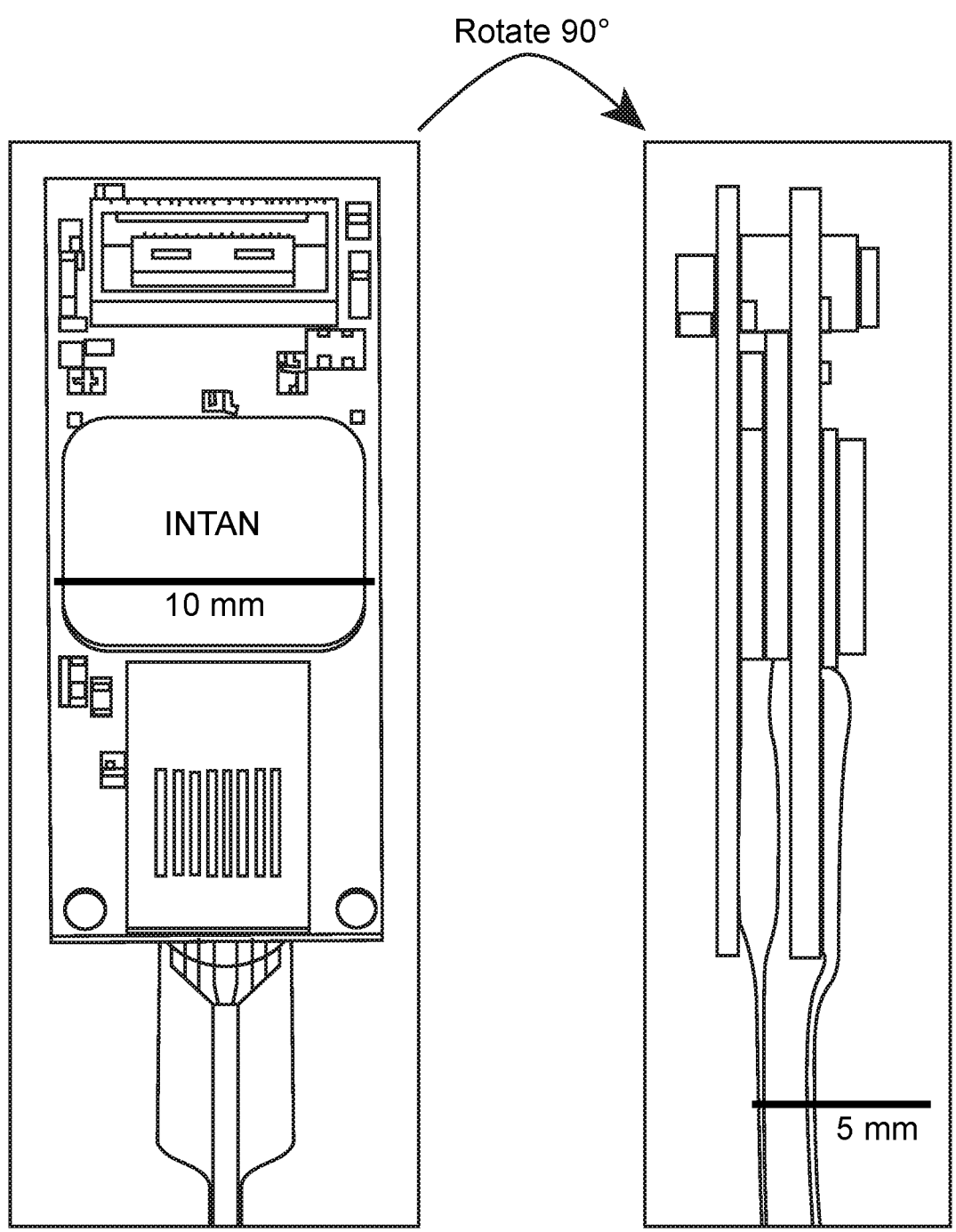
Figure 2:
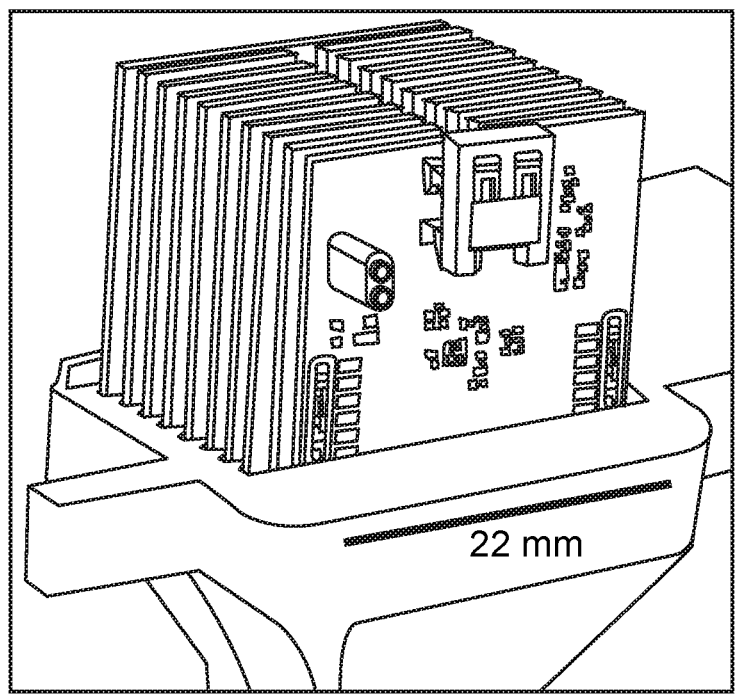
Figure 2:
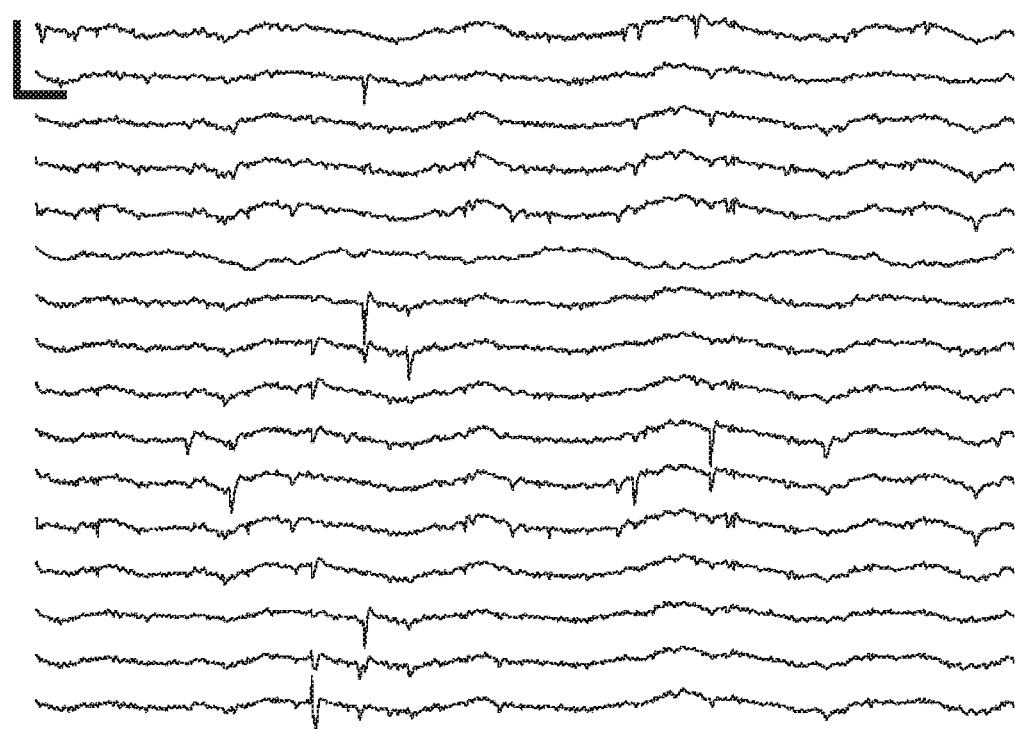

Devices with a 4-shank, 64-channel single-unit configuration are diagrammed in FIG. 2, Panel B with an edge-of-shank to edge-of-shank distance of 250 μm (center-of-shank to center-of-shank distance or pitch of 330 μm). This design was used in the 1024-channel rat implant, and one module was used in a 352-channel implant (one 4-shank 64-channel module alongside six 2-shank 32-channel arrays, and 24 tetrodes).

Devices with a 2-shank, 32-channel single unit configuration had an identical shank layout to the 4-shank configuration with the notable reduction in edge-of-contact to edge-of-shank distance from 12 μm (4-shank design) to 6 μm (2-shank design). This device design was used for the majority of the data shown, used in the 128-channel implant (data shown in FIG. 4, Panels A-D), and all 288-channel implants (six, two-shank, 32-channel polymer arrays and 24 tetrodes).

The device with a 2-shank, 36-channel single-unit configuration (featured in FIG. 5, A-C) had a dual-line, staggered design to the other single-unit configurations. The shank width was 100 μm, edge-of-contact to edge-of-shank distance was 12 μm, and 3 of the 18 contacts were placed closer to the tip of the shank.

PEDOT-PSS Application and Site Impedance

The solution used for PEDOT-PSS application consisted of 0.14% by weight 3,4-ethylenedioxythiophene (EDOT) and 0.08% by weight poly(sodium 4-styrenesulfonate) (PSS) in deionized water. Constant current was applied to microelectrodes for PEDOT-PSS deposition at a current density of 3 mA/cm$^2$ for 50 seconds.

The typical impedances of the 20 μm circular contacts after PEDOT-PSS deposition was less than 100 kOhm at 1 kHz measured in-vitro in the following manner. Electrochemical impedance (EIS) measurements were made using a potentiostat (Princeton Applied Research, AMETEK Inc.) using vendor-supplied software. All measurements were made in a three-electrode cell using a Pt counter electrode, an Ag/AgCl reference electrode, and phosphate-buffered saline (pH 7.5) as the electrolyte.

Silicon Stiffeners

The silicon stiffeners had different dimensions than the polymer arrays that they were coupled to. The stiffeners were 30 μm thick and 60 μm wide and centered relative to the 80 μm wide polymer array shanks. This was done to help prevent overflow of the polyethylene glycol from the bond interface to the top of the polymer array. The array and stiffener were both aligned at their tips, although the stiffener had a sharper tip angle of 25° compared to the polymer array's tip angle of 45°.

Preparation of Stiffeners and Arrays for Insertion

Polymer arrays had a 2 cm long×1 mm thick strip or tube of polyimide attached perpendicular to the length of the array, 10-20 mm above the shank tips using UV curable epoxy (Loctite 3974, Henkel). This strip of polyimide was later used for tethering the probe to the implant.

The silicon stiffener and polymer array were bonded together using PEG. This involved PEG application to the silicon stiffener's reservoir and heating of the stiffener using a hot plate. The PEG wicked down the channel etched into each shank of the stiffener. Next, the stiffener and array were aligned such that the tips were overlapping and the array's shanks were centered relative to the stiffener. The stiffener-probe device was then allowed to cool and the PEG bonded them together. Next, a drop of PEG was placed on top of the polymer probe and silicon stiffener, 2 to 4 mm above the top of the shanks.

The stiffener was fixed to a custom 3D-printed insertion piece (RGD837 Stratasys, MN) using an ethyl cyanoacrylate-based adhesive (Loctite 1363589, Henkel) and the Omnetics connector or PCB bonded to the polymer array was attached to a second custom 3D-printed insertion piece (RGD837 Stratasys, MN). The two 3D-printed pieces were connected using a screw. Once affixed to the 3D-printed insertion pieces, the stiffener and array were sterilized using ethylene oxide (Anprolene AN74i, Andersen products).

16-Module, 1024-Channel Implant

The 16-modules were distributed equally across both hemispheres. Of the 16 modules implanted, 2 were targeted to dHPC. These two arrays were designed for sampling local field potentials and had an electrode pitch of 100 µm (center-to-center distance of 100 µm) with 20 µm circular contacts. Data from these arrays were not used for spike sorting. Of the remaining 14 modules, 4 were targeted to OFC, 4 were targeted to VS, and 6 were targeted to mPFC. Of the 6 devices targeted to mPFC, 4 were implanted too superficially. There were device failures on 2/4 targeted to VS, with one module having an intermittent connection and one module having highly correlated signal, possibly due to a short at the level of the polymer or the PCB.

160 Day Periodic Recordings

Polymer probes were targeted to mPFC or OFC. In one implant, two two-shank 36-channel arrays were implanted into mPFC and recorded from for 263 days, the termination of the experiment due to animal approaching end of life expectancy. This animal was recorded from using the NSpike data acquisition system (L. M. F. and J. MacArthur, Harvard Instrumentation Design Laboratory) in a 13"×13" rest box, and was returned to its home cage. The second implant consisted of four 2-shank 32-channel arrays, all targeted to OFC (128-channel implant). The third animal was implanted with six 2-shank 32-channel polymer arrays targeted to mPFC, alongside two stimulating electrodes targeted to vHC, and 24 tetrodes targeted to dHPC bilaterally, for a total of 288-channels of recording. For the longevity analyses, the second and third animals were also recorded from in a 13"×13" rest box, but on some unanalyzed days, recordings were also carried out while the animal ran in a spatial environment.

10-Day Continuous Recording in mPFC

Three animals were implanted with six, two-shank, 32-channel polymer arrays targeted to mPFC, alongside two stimulating electrodes targeted to vHC, and 24 tetrodes targeted to dHPC bilaterally. One of the three animals also had one four-shank, 64-channel polymer array targeted to right OFC. This same animal had a device failure resulting in two functional 32-channel polymer arrays in mPFC and one 64-channel polymer array in OFC. Another animal had a commutator failure on day 4 of recording, causing intermittent data loss, and firing rates from this animal's day of recording were not used for firing rate analyses. Recordings were carried out while animals were housed in their home cages and in alternating epochs of exposure to a familiar rest box and one of two spatial environments in different rooms. Data were not collected when the animal was being moved between rooms with gaps in recording of 15 to 20 minutes in length, with one instance of a 45-minute gap when the commutator failure was discovered. Animals ran 600-1000 meters per day in these spatial environments and provided a challenging experimental setting in which to assess recording stability.

On the first day of continuous recording, animals stayed in one room, room A, where they had been performing the same spatial task for several weeks, and performed three behavioral sessions, each lasting 30-40 minutes. On the second day of recording, animals performed two 30-40 minute behavioral sessions in room B, their first time being exposed to that room, and then one in room A. On days three through eleven, animals performed two or three sessions of behavior in room B followed by one in room A. Recording was stopped half an hour after the animal finished the session of behavior in room A on day eleven (animals A and B), or day twelve (animal C). In animal C, a twelfth day of recording was carried out with all behavioral sessions occurring in room A. Animals had red/green tracking LED arrays attached to the implant, allowing their position to be extracted from video recorded by a camera mounted to the ceiling.

Histology

Subjects were euthanized with pentobarbital and intracardially perfused with PBS followed by 4% paraformaldehyde in PBS. The brain was post-fixed in situ overnight, after which the brain was removed, cryo-protected (30% sucrose in PBS), and embedded in OCT compound. Coronal sections (50 µm) were taken with a cryostat. Sections were stained with NeuroTrace 435/455 Blue Fluorescent Nissl Stain (1:200; Invitrogen, N21479, lot 1846588). Sections were blocked (5% donkey serum in 0.3% Triton-X in PBS, used for all incubations) for 1 hour, incubated with Monoclonal Anti-Glial Fibrillary Acidic Protein (GFAP, 1:800, Sigma-Aldrich, G-3893, mouse, clone G-A-5, lot 31K4885) overnight, washed, and subsequently incubated with fluorescent secondary antibody (Alexa Fluor 488, 1:400, Thermo Fisher Scientific, Z25002).

Data Processing and Analysis

Data analysis was performed using custom software written in Python 3.6.3 (Anaconda linux-64 v7.2.0 distribution, Anaconda Inc.) and Matlab 2015b (Mathworks).

Spike Sorting

Clustering was done using MountainSort, using settings and thresholds as reported previously (Chung et al., 2017). Adjacency radius was set to 100 µm when sorting the 20 µm contact, 20 µm edge-to-edge dual-line designs, resulting in clustering neighborhoods of 5 to 9 electrodes. The event detection threshold was set to 3 SD. Putative single-units were identified using previously set thresholds (isolation >0.96, noise overlap <0.03) and an automatic merging procedure, reported previously (Chung et al., 2017), was used to identify pairs of clusters that corresponded to the higher and lower amplitude components of single units that fired in bursts with decrementing spike amplitudes.

The first step in processing the 240-hr continuous recording datasets was filtering and spatial whitening the entire 240-hr timeseries. Following this, events were detected and clustered in 24-hour segments. Automated curation and bursting-related merging was first completed independently for each segment. As a result, all clusters in all segments satisfied our criteria for well isolated units. Linking clusters between segments was done using a mutual nearest neighbor rule. For every cluster in the first segment, a 1.66 ms spatially-whitened waveform template was calculated from the last 100 events, using every channel on the shank. Similarly, for every cluster in the second segment, a waveform template was calculated from the first 100 events. Next, the $L^2$ distance was calculated between every segment 1 and segment 2 pair of templates. If cluster A from segment 1 and cluster A' from segment 2 were mutual nearest neighbors, then the segments were linked.

This approach was conservative as a result of three main features. First, it used only well isolated clusters from each segment, and only matched these well isolated clusters. Second, because the 24-hour segments were not aligned to specific events in the animals' experience, the segments partitioned the spiking activity at points where large, sudden changes in spike amplitudes were very unlikely. Third, the distance calculation was based on whitened spike waveforms from the entire 16 electrode array, yielding unique templates for each unit. The mutual nearest neighbor calculation ensured that these templates matched across the segment boundaries, and that this linking algorithm was found to yield plots of spike amplitude over time that were continuous across the period where the unit could be tracked.

SWR Detection and Modulation

SWRs were detected as previously described (Cheng and Frank, 2008). Briefly, LFPs from a contact near CA1 was filtered into the ripple band (150-250 Hz) and the envelope of band-passed LFPs was determined by Hilbert transform. SWR were initially detected when the envelope exceeded a threshold (mean+3 SD) on the contact. SWR events were defined as times around the initially detected events during which the envelope exceeded the mean. For SWR-triggered firing rates, only SWRs separated by at least 500 ms were included.

SWR modulation analysis was carried out as described previously (Jadhav et al., 2016). Briefly, spikes were aligned to SWR onset resulting in SWR-aligned rasters. Cells with less than 50 spikes in the SWR-aligned rasters were excluded from these analyses. To determine the significance of SWR modulation, 1,000 shuffled rasters were created by circularly shifting spikes with a random jitter around each SWR and defined a baseline response as the mean of all shuffled responses. The mean squared difference was calculated between the response in a 0-200 ms window after SWR onset (SWR response) to the baseline. The real SWR response was compared to the 1,000 shuffled responses. A cell was considered as SWR-modulated when the mean squared difference of the SWR response from the baseline was greater than 95% of the shuffled PSTHs. SWR-modulated neurons were further categorized as SWR-excited or SWR-inhibited by comparing the rate in a 0-200 ms window after SWR onset, with the rate of the mean shuffled response in the same 0-200 ms window.

Generalized Linear Models During SWRs

Construction of generalized linear models (GLMs) was done as reported previously (Rothschild et al., 2017). The GLMs were constructed with a log link function to predict spike counts of single units during SWRs in PFC, NAC, or OFC from ensemble spiking patterns in another region. The region's SWR ensemble pattern was the vector of binned spiking responses across units recorded in that region during the 0-200 ms window after SWR onset.

The ensemble patterns were used to predict single cell SWR responses. A single prediction model was generated using predictor data of the ensemble patterns across SWRs, and predicted data of the single-cell SWR responses across SWRs. Only cells that were active (>0 spikes) in more than 10 SWRs were predicted. For each predictor ensemble and predicted cell, five-fold cross validation was performed. The SWRs were randomly partitioned into five equally sized sets, with the constraint that the number of nonzero values in the predicted vector must be approximately balanced across sets. For each fold, four of five folds were used to train the GLM, and the remaining folds used to test. For the test phase, the model derived from the training phase was applied to the predictor ensemble data in the test set, yielding predictions for the predicted cell firing across SWRs.

Prediction error was defined as the mean absolute difference between the predicted spike counts and the real spike counts. For that same fold, a baseline prediction error was defined by performing 100 random shuffles of the predicted firing rates across SWRs in the test fold and taking the mean of the shuffled prediction errors. The real and shuffled prediction errors were then averaged across the five folds. Prediction gain for one predictor-ensemble-predicted-cell combination in one time window was defined as the shuffled prediction error divided by the real prediction error.

For comparison, the exact same procedure was repeated described above on 100 random shuffles of the entire original dataset, where shuffling entailed random matching of activity patterns in the predictor and predicted data (e.g., taking predictor data from one SWR and using it to predict firing rate for another SWR). To assess prediction significance for a pair of regions, the distribution of real prediction gains was compared to the shuffled prediction gains across all ensemble/cell combinations using a two-tailed nonparametric Wilcoxon rank sum test.

Cluster Linkage Analysis

Quantification of the relative distances of successfully linked cluster pairs to the other possible linked clusters (FIG. 7, Panel A) was done as follows: if there was a successful link made between cluster A from segment 1 and cluster A' from segment 2 (A to A'), then the $L^2$ distances between cluster waveform templates (A and B'), (A and C'), ... (B and A'), (C and A'), etc., were normalized to the $L^2$ distance of (A to A'). These distances, for all successfully linked pairs across all electrode arrays, contributed to the histogram in FIG. 7, Panel A.

To quantify the distances of successfully linked cluster pairs and their distance to other possible linked clusters relative to the variability of the events within the successfully linked cluster, the same set of distances was normalized as above using the mean spike distance to its template. Specifically, if there was a successful link made between cluster A from segment 1 and cluster A' from segment 2 (A to A'), the mean of the $L^2$ distances between the 100 events and the template of A (calculated from the same 100 events) was used as the normalization factor for the $L^2$ distance from (A to A'), and all other unlinked pairs, (A and B'), (A and C'), ... (B and A'), (C and A'), etc. This mean of the $L^2$ distances is referred to in the text as "event distance."

Figure 7:
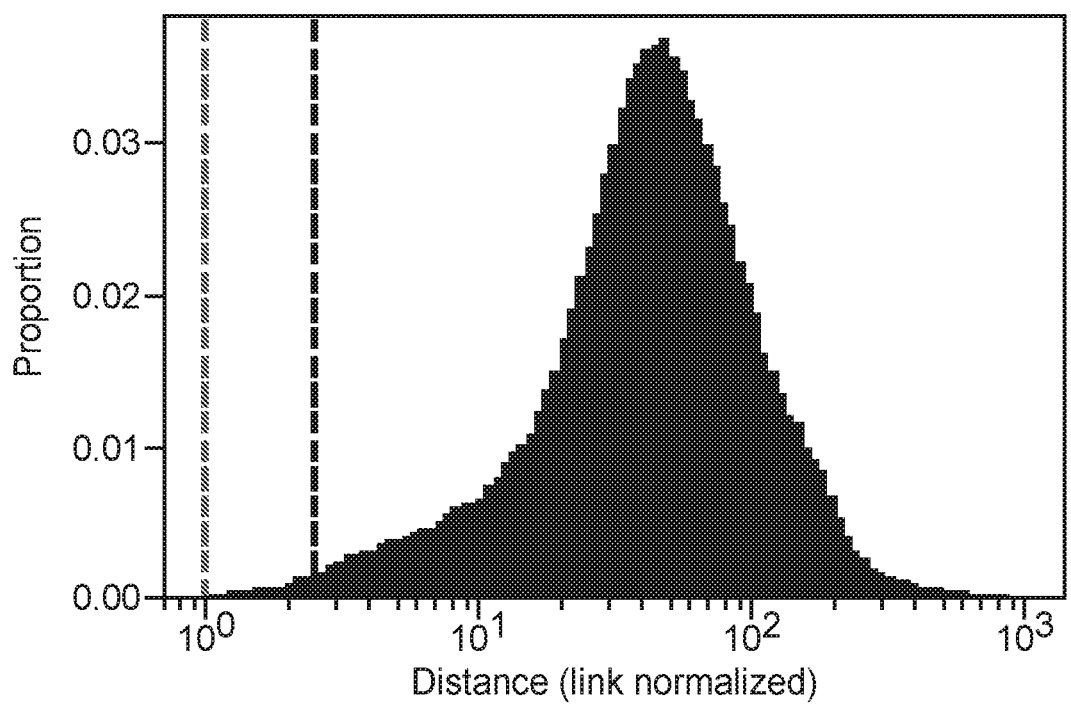
FIG. 7, Panels A-E depict the validation of cluster linkage and stability of single units.
Figure 7:
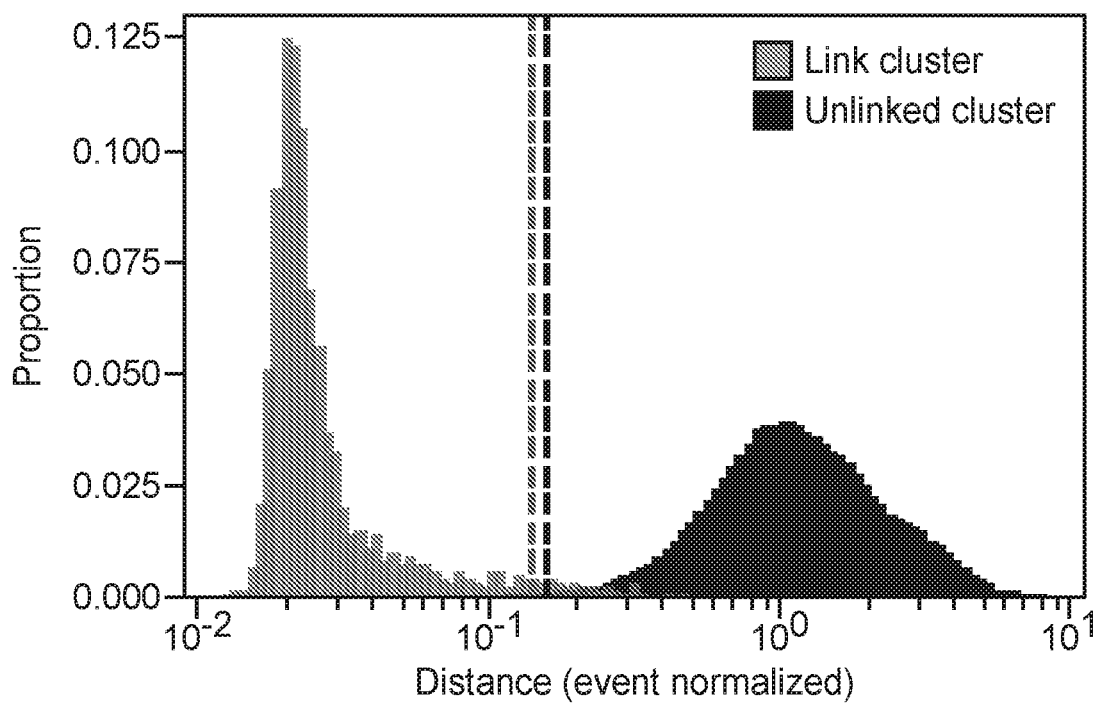
Figure 7:
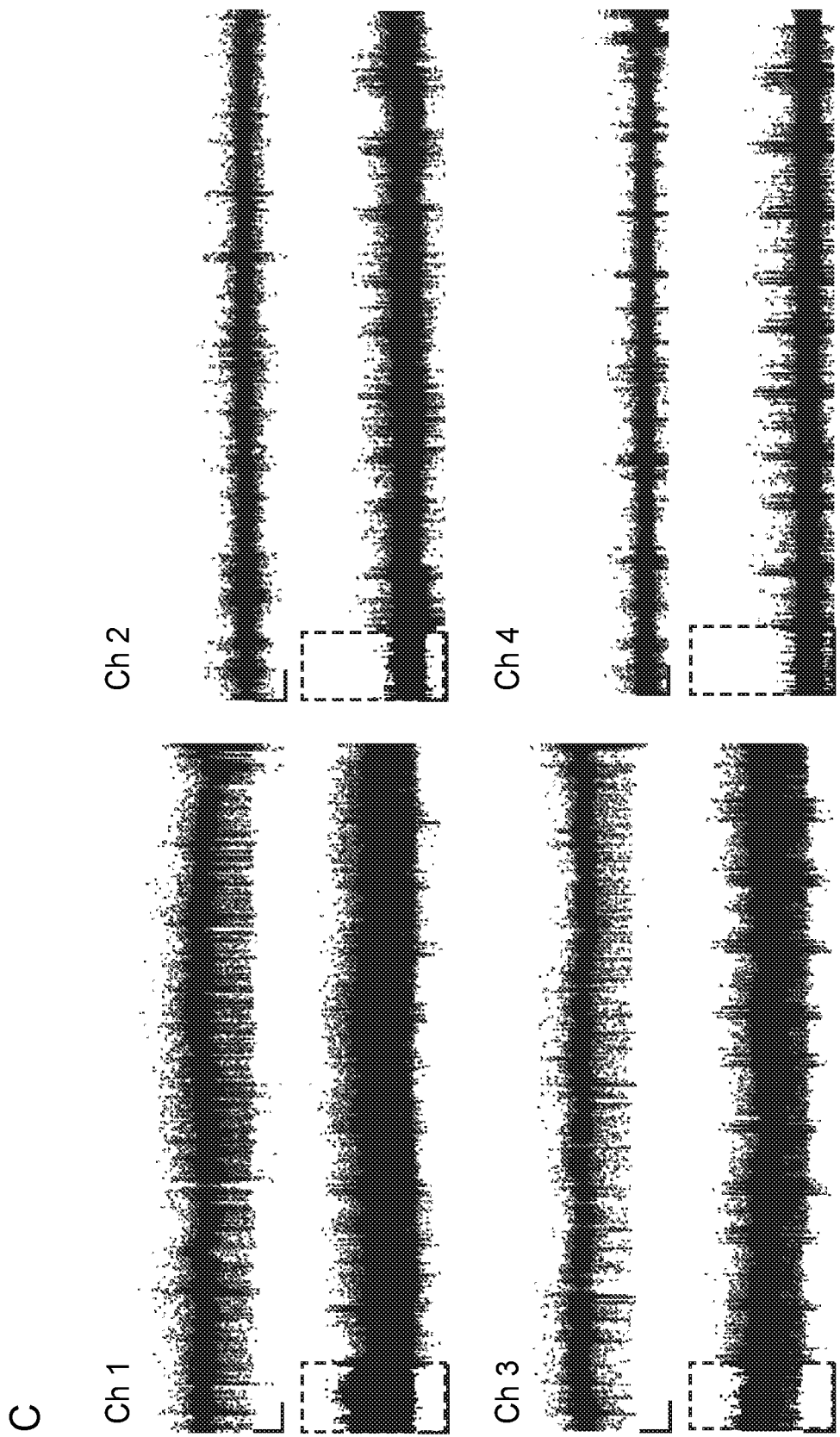
Figure 7:
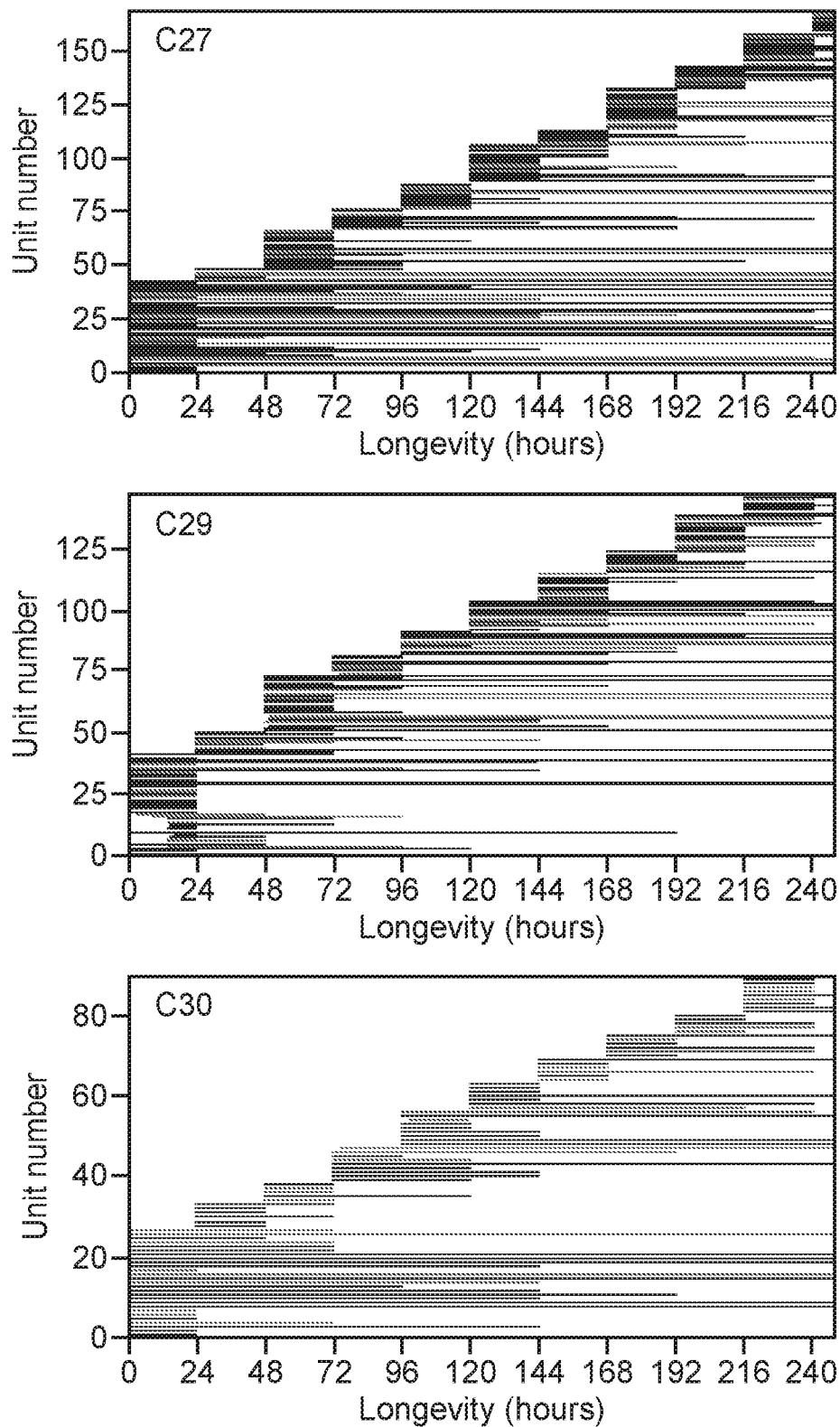
Figure 7:
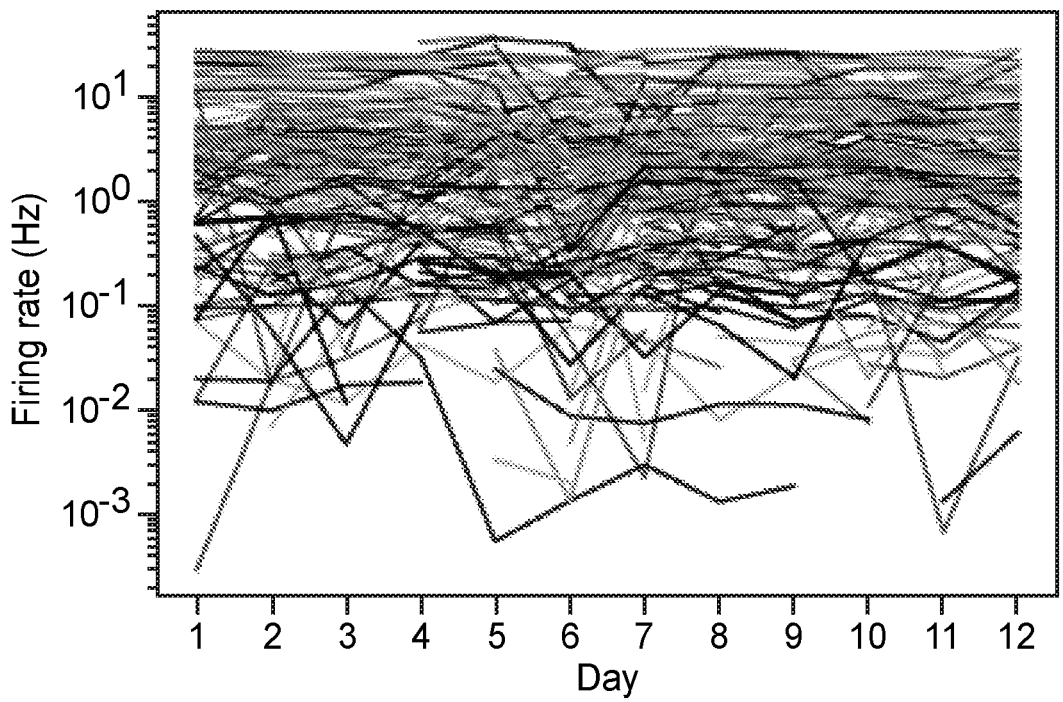
Figure 7:
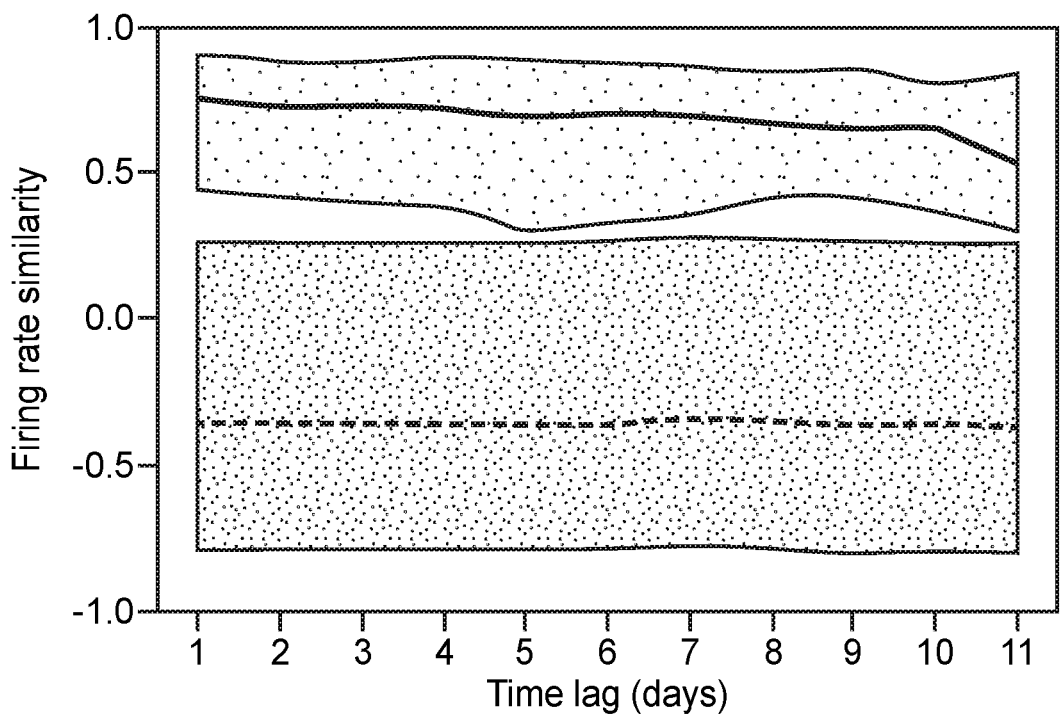

In FIG. 7, Panel B, the normalized distances of successful linkages, (A to A'), contributed to the histogram in red, while the normalized distances of all other unlinked pairs, (A and B'), (A and C'), (B and A'), (C and A'), etc., contributed to the histogram in black.

Firing Rate Similarity During Behavioral Performance

Firing rates were calculated for when the animal was performing the spatial behavior in room A. This constituted ~90 minutes of time on day one (and day twelve in animal C), or ~30 minutes of time on days two through eleven. Roughly half of the time during behavioral performance was spent either at low (<4.0 cm/s) or high (≥4.0 cm/s) velocities.

Firing rate similarity was calculated using the same formula as in (Dhawale et al., 2017), where the similarity of two different firing rates, $FR_i$ and $FR_j$ was measured by the following formula:

$$FR\text{similarity}_{i,j} = \frac{\text{abs}(FR_i - FR_j)}{FR_i + FR_j}$$

A firing rate similarity score of 1 occurred when $FR_i$ and $FR_j$ were identical, and a firing rate similarity score of −1 occurred when one firing rate was 0 (maximally dissimilar). When comparing firing rates for the same unit across time, firing rate similarity was calculated for time lags ranging from 1 to 10 days (animals A and B), or 11 days (animal C), as depicted in FIG. 7, Panels A-E. In other words, if a cell was tracked for all 12 days of behavioral performance in room A, its 1-day time lag firing rate similarity was calculated 11 times (days 1-2, 2-3, ... 10-11, 11-12), or its 10-day time lag was calculated twice (days 1-11, 2-12).

The distribution of within-unit time lagged similarities was compared to the distribution of all between-unit time lagged similarities, matched for both shank and time lag. This differed from the comparison done in Dhawale et al., 2017, where time-lagged similarities were compared to the within-day across-unit distribution of firing rate similarities.

Code Availability

Electrode-drift spike sorting code was available at https://github.com/magland/msdrift. This code was designed to be a package added to the core MountainSort software, available at https://github.com/flatironinstitute/mountainsort.

Results

Example 1: Modular Implantation Platform

Electrophysiological recordings provided millisecond resolution information about the activity of neurons, and the system described herein made it possible to access this information simultaneously across hundreds of neurons within a region, in multiple anatomically distant regions, and to do so for a time period spanning months. Large-scale recordings were demonstrated from neurons in three widely separated brain structures, the orbitofrontal cortex (OFC), the medial prefrontal cortex (mPFC), and the nucleus accumbens (NAc), yielding a conservative total of 375 well-isolated neurons recorded simultaneously. These recordings allowed the demonstration of widespread and coordinated activation of all three regions at the time of hippocampal sharp-wave ripple (SWR) events. Moreover, high quality recordings were obtained across many months. In addition, the polymer probe-based system made it possible to perform continuous 24/7 recording. Specifically, 2322 units were tracked for 24 hours or more, and 247 (of the 1150 possible, ~21%) of these units across more than a week.

The system made it possible to measure the activity of hundreds of single neurons across multiple, anatomically distant structures in freely-behaving animals. The system furthermore supported continuous 24/7 recording and yielded high quality, large-scale single unit recordings for at least five months. In conjunction with this recording system, the MountainSort (Chung et al., 2017) spike sorting system was adapted to link clustered units across time segments, demonstrating stable recordings from 21% of individual neurons for over a week. The system provided both high density and modularity to allow for recordings of many units across a set of structures of interest, and longevity and stability to study these units across behavioral states and as they evolved.

The flexibility of polyimide arrays increased biocompatibility. A detachable silicon stiffener insertion system was employed. The silicon stiffeners had a thickness of 30 μm and width of 60 μm, as well as a sharp tip angle of 25°. These features made for a low cross-sectional area and reduced trauma on insertion. Stiffener-attached arrays were inserted serially into brain tissue and subsequently tethered to a custom 3D-printed base piece, which was contoured and anchored to the skull (FIG. 1, Panels A-H). Serial insertion allowed multiple arrays to be placed within a single brain region (<1 mm between inserted probes). The rest of the implant was then assembled intraoperatively; silicone gel was added to stabilize the brain and formed a protective layer over the polyimide arrays. Silicone elastomer was added to protect the polymer arrays from damage and active electronic components from moisture. The entire system was then protected with a custom 3D-printed casing and passive aluminum heatsinks for impact resistance and heat dissipation (FIG. 1, Panels D-E).

The result was an implant that drew 1.48 watts (0.435 Amps at 3.4 V) and weighed 81 g, including 31 g dedicated to heat management, providing 0.0115 $m^2$ of surface area. During data collection, the temperature of the heat sinks was 41-42° C. (measured by IR thermometer, room ambient temperature 21° C.), only slightly above rat body temperature. After three weeks of recovery post implantation, the animal's movement was only mildly impeded by the weight and typically ran 400-600 meters per day when performing spatial behaviors.

FIG. 1, Panels A-B depict top-down views of a rat skull with 3-D printed implant base attached before polymer array insertion (FIG. 1, Panel A), and after insertion of 7 polymer probes (FIG. 1, Panel B). FIG. 1, Panel C depicts a magnified view of polymer probes entering into brain. FIG. 1, Panel D depicts a cross-sectional schematic of implant after arrays have been inserted and silicone gel has been added to the 3-D printed base, and of the assembled implant (FIG. 1, Panel E), with silicone elastomer fill to protect soft passive electrical components and moisture-sensitive active electrical components, and to provide strain relief for their soft-hard interface. FIG. 1, Panel F depicts a 3D model of active electronics (red) and casing (grey), which provide structural support and protection for the passive electrical connection from the implanted contacts to the active electronic components. FIG. 1, Panel G depicts a 3D model of full implant with polymer probe (cyan), single 64-ch board module (green), active electronics and micro-HDMI cable (red). FIG. 1, Panel H depicts a rat implanted with full system, including heat sinks (black) and silicone grommets for impact resistance (cyan).

Simultaneous, large-scale single-unit recording in a distributed neural circuit required that recording electrodes be flexibly distributed across the brain, and at high enough density to yield hundreds of putative single neurons. In the past this necessitated a choice between a few high-density arrays with rigid geometries, or many lower-density arrays (or single channels) that could be arbitrarily and precisely distributed across the brain. The approach described herein, outlined in FIG. 2, Panel A, reduced the need for this tradeoff, allowing for high-resolution sampling across multiple targeted regions.

Multishank polyimide electrode arrays formed the modular implantable unit, fabricated using a process described previously (Tooker et al., 2012b, 2012a). Each 32- or 64-channel array utilized a new design for single-unit recording in rat cortex, having two or four shanks respectively, with 16 channels per shank in a dual-line layout (FIG. 2, Panel B). Each recording contact included a platinum electrode covered by electrically deposited PEDOT-PSS. Each 32-channel device had an attached 32-channel Omnetics connector, two of which were accommodated by the pair of mating connectors on each custom printed circuit board (PCB). The same PCB had a readily-available 64-channel amplifying, digitizing, and multiplexing chip (INTAN technologies) wire-bonded to it. An alternative 64-channel PCB replaced the Omnetics connectors with ENEPIG plated pads where the 64-channel arrays were directly wire bonded to the PCB. The resulting modules (FIG. 2, Panel C) were stacked using mezzanine connectors and connected to a custom field programmable gate array (FPGA, SpikeGadgets LLC) which supported up to two stacks of eight modules, for a total of 1024 channels (FIG. 2, Panel D). The stacking modules and FPGA were the core hardware of the recording system described herein. The FPGA synchronized the modules and converted the serial peripheral interface bus (SPI) signal from each module to high-definition multimedia interface (HDMI) format, allowing the use of consumer hardware. The 1024 channel, 30 KHz/channel data were streamed via a micro-HDMI cable through a low-torque HDMI commutator (SpikeGadgets LLC) and data acquisition main control unit (MCU, SpikeGadgets LLC) to the data acquisition computer where it was visualized and saved (FIG. 2, Panel E). Streaming high speed data through a HDMI commutator enabled robust continuous recordings.

FIG. 2, Panel A depicts a data path from electrode to computer, with box color corresponding to related components in following subfigures. FIG. 2, Panel B depicts a polymer electrode array with a schematic of a 16-channel shank of polymer array designed for single-unit recording (FIG. 2, Panel B, left). All contacts are circular with 20 µm diameter with 20 µm edge-to-edge spacing. A shank is 14 µm thick. FIG. 2, Panel B, middle-left depicts an image of a 16-ch shank. FIG. 2, Panel B, middle-right depicts a 4-shank (250 µm edge-to-edge spacing), 64-channel array. FIG. 2, Panel B, right depicts a full polymer array, bond pads at top of array. FIG. 2, Panel C, left depicts a view of individual 64-channel module with amplifying, digitizing, and multiplexing chip (Intan Technologies) wire-bonded onto board, and mezzanine-style connector attached at top of board. FIG. 2, Panel C, right depicts two modules stacked together. FIG. 2, Panel D depicts a full 1024-channel, 16-module, recording system stacked into FPGA headstage (SpikeGadgets LLC) during implantation. FIG. 2, Panel E depicts raw 100 ms traces from one 16-ch shank. Scalebar corresponds to 1 my vertically and 5 ms horizontally.

Figure 3:
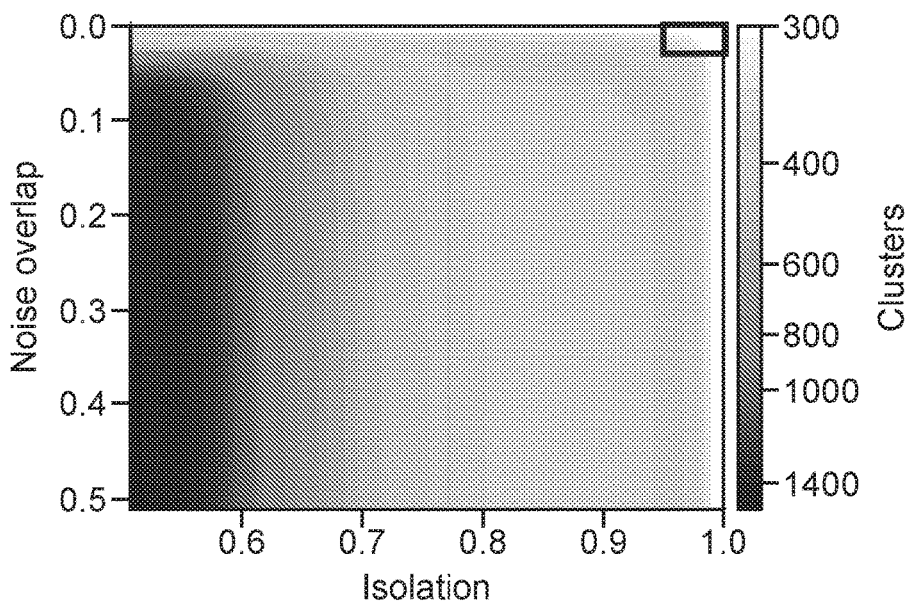
FIG. 3, Panels A-F depict the results of large-scale, distributed recordings using the methods described herein.
Figure 3:
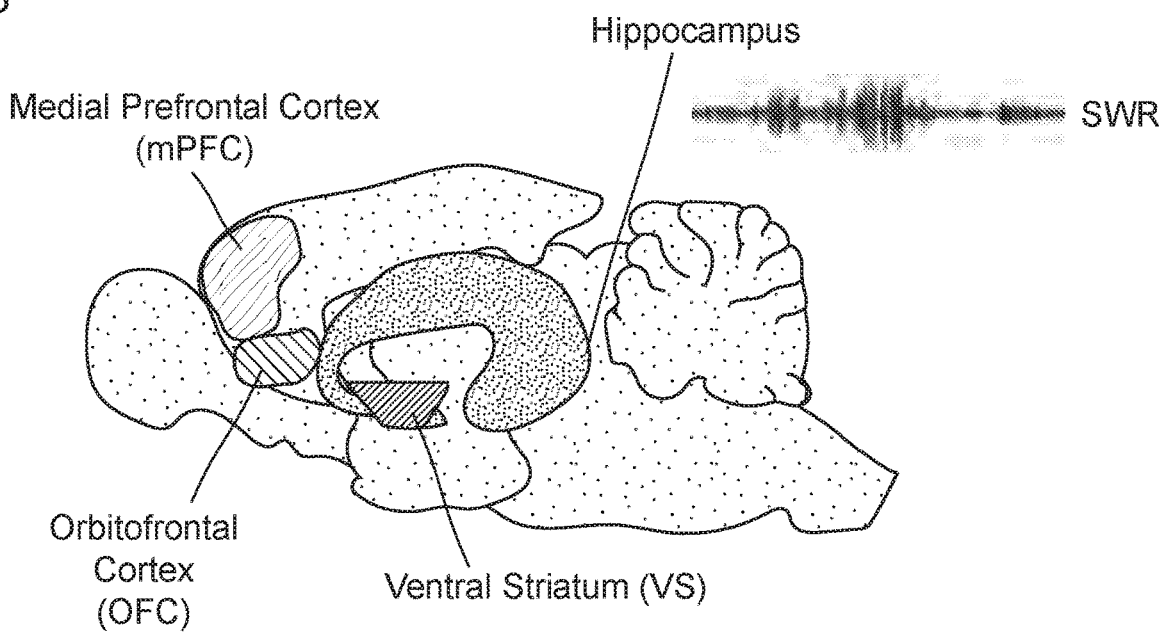
Figure 3:
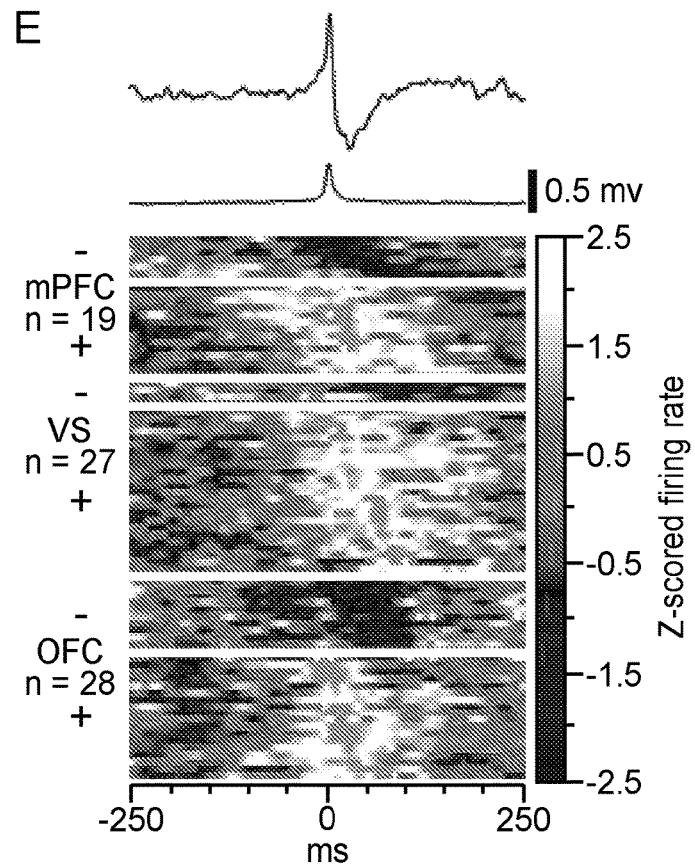
Figure 3:
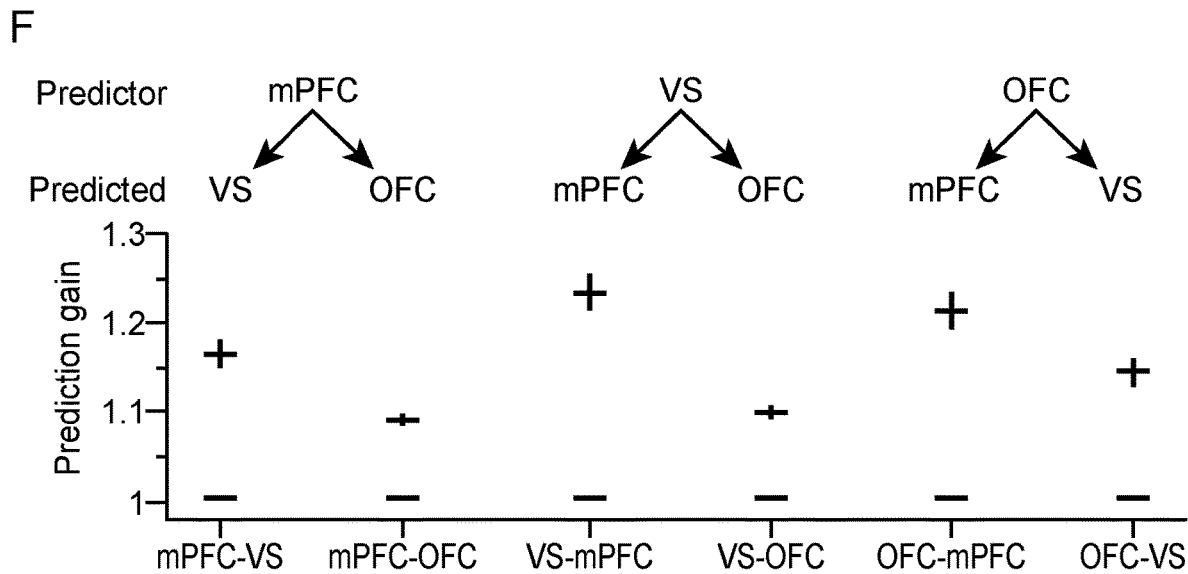

Example 2: Recordings of Hundreds of Single Units Distributed Across Multiple Regions Information processing in the brain depended on the millisecond-timescale interactions of large populations of single neurons distributed across multiple regions. To demonstrate the platform's ability to resolve network events spanning multiple regions, data were examined from an animal implanted with the full 16-module system. Of these, 8 modules were used for single-unit recording, 2 modules were used for local field potentials, and the remaining 6 had a device or implantation failure (4 were implanted too superficially, 1 module had an intermittently connected headstage chip, and 1 had low-quality and highly correlated signal of unknown cause, see methods for more details). Data were collected during a rest period in a familiar environment. Spike sorting using MountainSort (Chung et al., 2017) on data from these 512 channels 45 days after implantation produced 1533 clusters with a continuum of qualities. The clusters were then stratified using our previously established (Chung et al., 2017) k-nearest neighbor-based cluster quality metrics, isolation and noise overlap. These per-cluster metrics relied on the proportion of that cluster's events whose nearest neighbor was from the same cluster versus another cluster (isolation) or an empirically generated noise cluster (noise overlap). Three hundred seventy five of the 1533 clusters exceeded our previously established (Chung et al., 2017) thresholds (isolation >0.96, noise overlap <0.03), and were henceforth considered single units (FIG. 3, Panel A). The modules used for single unit recording were distributed among medial prefrontal cortex (mPFC, n=2 modules), orbitofrontal cortex (OFC, n=4 modules), and ventral striatum (VS, n=2 modules), and polymer probes designed for recording local field potentials (LFP) were targeted to the hippocampus (HPC, n=2 modules) (FIG. 3, Panel B).

FIG. 3, Panel A depicts a number of putative single-unit clusters from 512 channels (of the 1024-channel implant), stratified by quality metric thresholds. Automated curation using MountainSort (noise overlap 0.03, isolation 0.96, black box in upper right) resulted in the identification of 375 single units from the 512 channels. FIG. 3, Panel B depicts a schematic of the rat brain with targeted regions highlighted.

Example 3: Coordination Across Multiple Regions During Hippocampal Sharp Wave-Ripples The simultaneous recording of single units across multiple regions made it possible to examine cross-area coordination. To illustrate the power of this approach for the study of distributed brain events, times of hippocampal sharp wave-ripples (SWRs) were detected. The SWR was a correlate of synchronous hippocampal population firing implicated in memory consolidation, memory retrieval and planning, and was known to engage activity across the majority of the brain. These earlier studies (Logothetis et al., 2012; Khodagholy et al., 2017) leveraged methods that had large spatial coverage but were lacking in single-unit resolution. Complementary studies utilizing dual-site recordings revealed that neurons across many cortical (Chrobak and Buzsaki, 1996; Sirota et al., 2003; Isomura et al., 2006; Ji and Wilson, 2007; Jadhav et al., 2016) and subcortical regions (Dragoi et al., 1999; Pennartz et al., 2004; Lansink et al., 2009) showed changes in firing rates around the time of SWRs, and that the specific set of active hippocampal neurons during each SWR could predict the set of active cortical neurons, indicating hippocampal-cortical coordination (Jadhav et al., 2016; Rothschild et al., 2017; Yu et al., 2017).

These findings suggested the possibility of brain-wide coordination at the time of SWRs, but whether these events engaged coordinated populations across multiple regions outside the hippocampus remained unknown. Activity patterns across the mPFC, VS and OFC were examined during SWRs. Changes in activity across the population of 375 single units were evident during individual SWRs (FIG. 3, Panels C-D). Across all SWRs, these changes resulted in significant increases and decreases in firing of a subset of units in each region (FIG. 3, Panel E). 19 of 61 mPFC ($p<1.0e-4$ as compared to expected proportion, z-test for proportions) and 27 of 118 NAc units ($p<1.0e-4$, z-test for proportions) showed SWR modulation based on a $p<0.05$ threshold (see methods). Of the 19 modulated mPFC cells, 13 were positively modulated and 6 were negatively modulated. Of the 27 modulated NAc units, 24 were positively modulated and 3 were negatively modulated. In addition, 28 of 196 OFC units were SWR-modulated ($p<1.0e-3$ z-test for proportions). Of the 28 modulated OFC units, 18 were positively modulated and 10 were negatively modulated, providing a further confirmation that SWR events engaged activity across many cortical and sub-cortical regions.

The large number of simultaneously recorded single units made it possible to show that spiking patterns are coordinated across multiple regions during SWRs. Cross-validated generalized linear models (Rothschild et al., 2017) were used to determine whether ensemble firing patterns in mPFC, NAc, or OFC could significantly predict the firing rate of individual cells in the other regions at the times of SWRs (FIG. 3, Panel F, see Materials and Methods). This prediction was highly significant for all pairs of regions (prediction gains reported as mean±standard error and p-values were from two-tailed Wilicoxon rank sum test: mPFC predicting NAc, 1.16±0.01, shuffle 1.00±9.8e-5, p=1.7e-74; mPFC predicting OFC, 1.09±0.01, shuffle 1.00±9.1e-5, p=8.2e-116; NAc predicting mPFC, 1.23±0.02, shuffle 1.00±7.7e-5, p=1.5e-38; NAc predicting OFC, 1.10±0.01, shuffle 1.00±1.1e-4, p=2.1e-109; OFC predicting mPFC, 1.21±0.02, shuffle 1.00±3.2e-4, p=9.8e-37; OFC predicting NAc, 1.15±0.01, shuffle 1.01±4.5e-4, p=7.5e-54; FIG. 3, Panel E). Together, these findings illustrated the power of large-scale, distributed recordings and provided the first evidence of coordinated firing patterns across multiple regions during SWRs.

FIG. 3, Panel C, top depicts a 5 second raw LFP trace from one of 128 channels implanted into Hippocampus, centered on a SWR. FIG. 3, Panel C, middle depicts a 150-250 Hz filtered trace. FIG. 3, Panel C, bottom depicts spike rasters from 375 simultaneously recorded neurons from the same time period, with colors corresponding to the highlighted region, with a horizontal axis in ms. FIG. 3, Panel D depicts recordings with similar parameters as used in FIG. 3, Panel C, but for 1 second centered around the same event. FIG. 3, Panel E depicts averaged 500 ms traces for average LFP (FIG. 3, Panel E, top), power (FIG. 3, Panel E, middle, 150-250 Hz). FIG. 3, Panel E, bottom depicts a normalized firing rate, peri-SWR histograms for the significantly SWR-modulated neurons, separated by recording location, and ordered by time of trough or time of peak (calculated from 4,046 SWRs). FIG. 3, Panel F depicts a prediction gain for each set of regions. FIG. 3, Panel F, top depicts a predictor region, with arrow to predicted region below. Mean prediction gain (horizontal line)±standard error (vertical lines) for each predictor-predicted set of regions. Color of bar corresponds to each predicted region, as shown in FIG. 3, Panel B. Shuffled prediction gains shown in black. Each of the actual prediction gains was highly significantly greater than the shuffled gains (all p's<10e-10).

Example 4: Longevity of Single-Unit Recording

Figure 4:
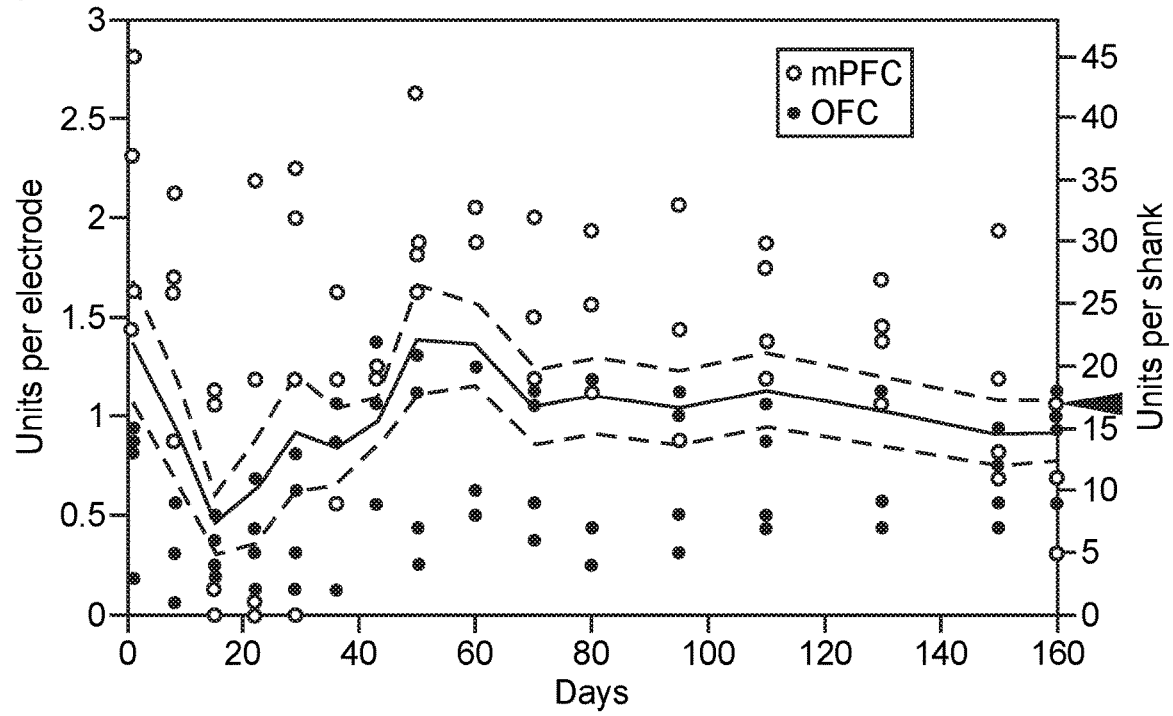
FIG. 4, Panels A-D depict single-unit recording yield of polymer probes over time.
Figure 4:
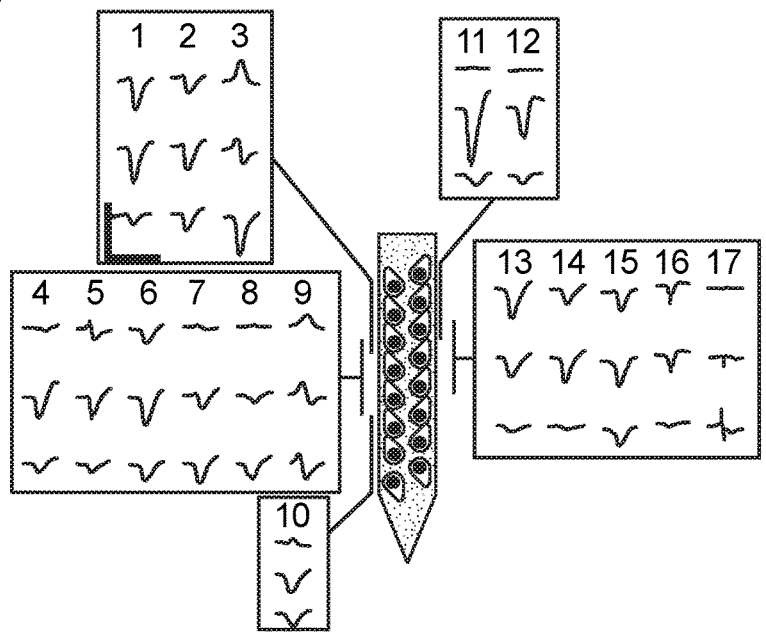
Figure 4:
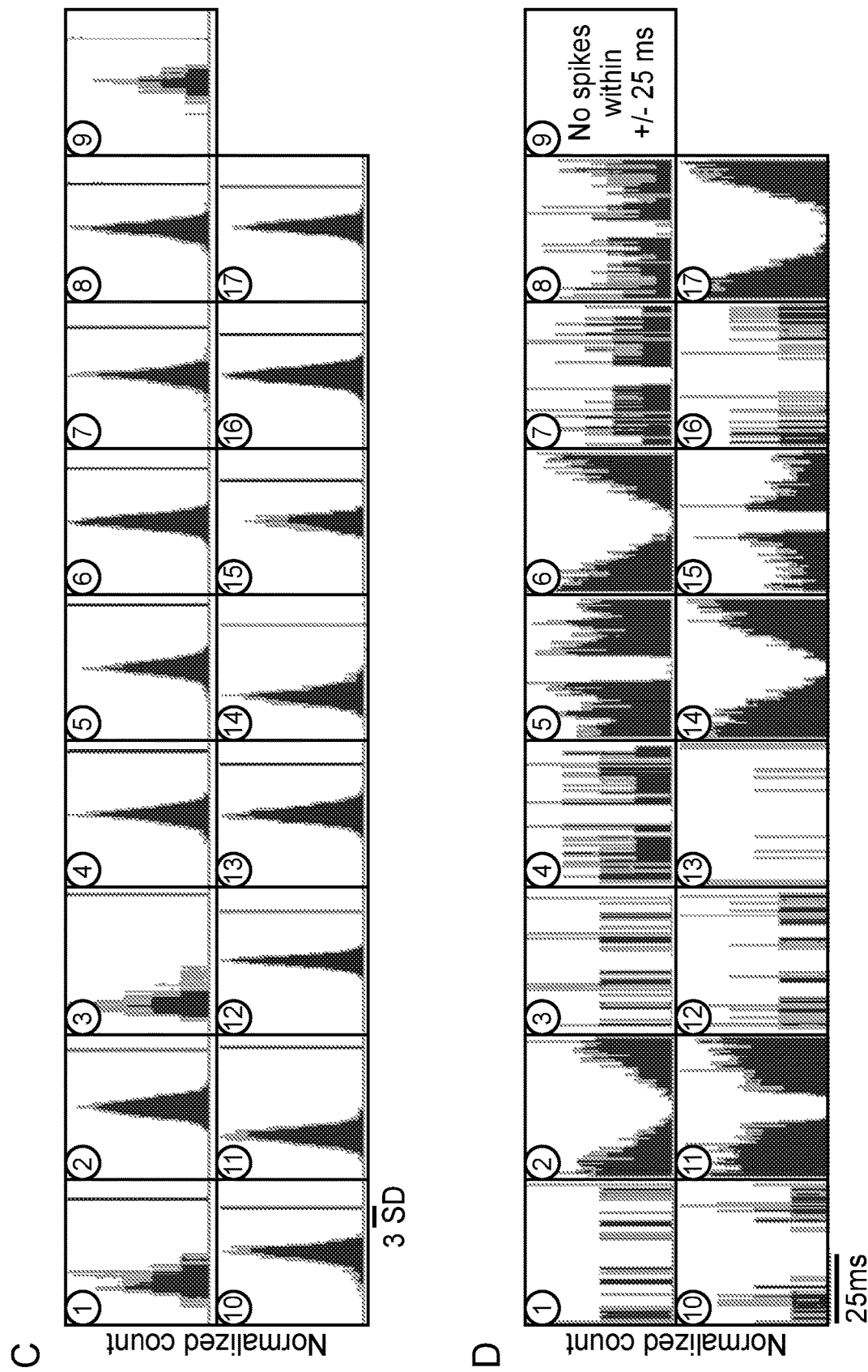
Figure 5:
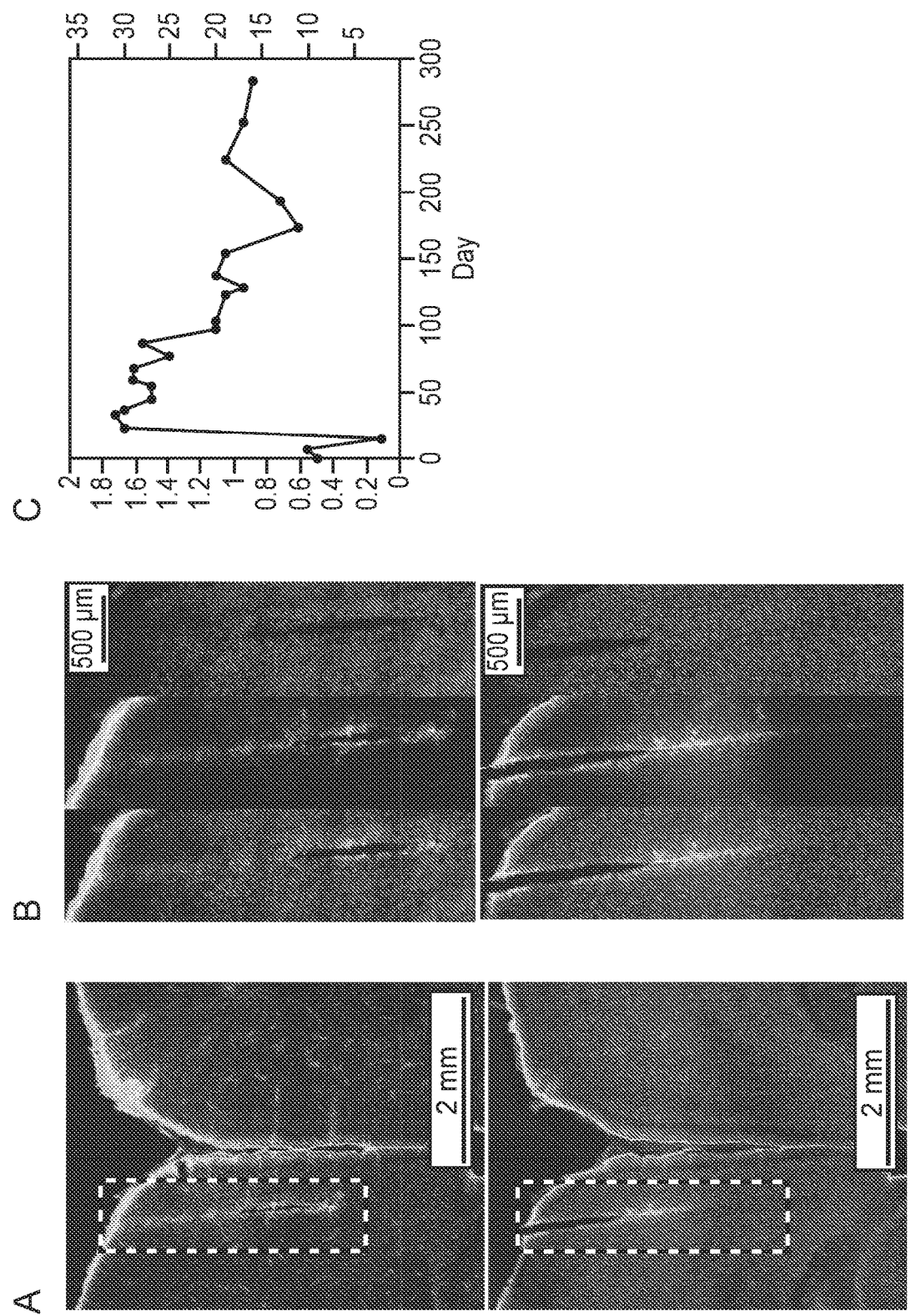
FIG. 5, Panels A-C depict the histology of the platform 160 days after implantation.

To evaluate the high yield single-unit recording capabilities of polymer arrays in the long term, three rats were implanted with polymer probes into mPFC or OFC and data were collected for 160 days or more (one 72-ch implant, one 128-ch implant, and one 288-ch implant). These implants yielded long-lasting, high-quality recordings (FIG. 4, Panel A), with some initial variability across a six-week timescale, consistent with the brain's recovery from an acute injury and the transition to a stable, chronic response (FIG. 5, Panel A-C). Subsequently, recording yield was stable until the end of recording (experiments terminated at 160 days to ensure the availability of histology), yielding up to 45 total units on an individual shank and ~1 single-unit per contact on average (FIG. 4, Panel A). Even after 160 days, the system continued to yield well-isolated individual single units (FIG. 4, Panel B), showing no sign of being truncated by the detection threshold (FIG. 4, Panel C) and having very few refractory period violations (FIG. 4, Panel D). In one case, the recordings were extended to 283 days and 16 single-units were isolated from the dataset collected on this final day, marking an end to a gradual decline in recording yield (from 27 single-units at day 45 post-implant to 16 single-units at 283 days post-implant; FIG. 5, Panel C).

FIG. 4, Panel A depicts single-unit yields for polymer probes per channel (left y-axis) or per 16-ch shank (right y-axis) over 160 days post-implantation (x-axis) in rats. Solid line is the mean cell yield across 8 shanks, dotted lines±1 SE. Individual time points per shank are shown as color-coded dots by region. FIG. 4, Panel B depicts waveforms and identification number for units clustered for data point with green arrowhead. Scale bar corresponds to 200 μv and 2 ms. Note that the root mean square voltage for the channels on this shank ranged from 15 to 17 μv, and thus all waveforms are substantially larger than the mean activity level. FIG. 4, Panel C depicts histograms of event amplitudes for units shown in FIG. 4, Panel B with unit identification number inset. Vertical black lines designate zero, with the vertical dotted lines representing ±3 SD, the detection thresholds. Scalebar corresponding to 3 SD and Y-axis normalized for each unit. FIG. 4, Panel D depicts spike autocorrelograms for the units shown in FIG. 4, Panels B-C, spanning ±25 ms and bin size of 0.5 ms. Scalebar corresponds to 25 ms and Y-axis is normalized for each unit.

FIG. 5, Panels A-C depict the histology corresponding to the shank with the arrowhead in FIG. 4, Panel A. FIG. 5, Panel A depicts merged images from adjacent 50 μm slices, with glial fibrillary acidic protein (GFAP) stain in green, and NeuroTrace (ThermoFisher Scientific) in blue. Note that region of separation of tissue is a result of tissue shrinkage during processing. FIG. 5, Panel B depicts similar histology as in FIG. 5, Panel A, but for highlighted regions: merge (FIG. 5, Panel B, left), GFAP (FIG. 5, Panel B, middle), and NeuroTrace (FIG. 5, Panel B, right). FIG. 5, Panel C depicts cell yields per channel (left y-axis) or per 18-ch shank (right y-axis) for a probe implanted for 283 days. Experiment was terminated due to animal approaching end of expected lifespan.

Example 5: Stability of Recording

The ability to track individual neurons across days depended upon stable recordings and a clustering strategy that was robust to changes in waveform shape resulting from electrode movement relative to neural tissue. Recording stability was evaluated following implantation of six 32-channel probes, each with two 16-channel shanks (192 of 288 total implanted channels) into each of three animals. Recordings were performed continuously (with the exception of moving animal between rooms) for 10 or 11 days (animal A, day 53 to 63 post-implant, animal B, day 47 to 57 post-implant, animal C, day 42 to 53 post-implant). Animals performed a spatial navigation task three to four times daily, running ~250 meters during each session. Behavioral sessions were performed in two different rooms. Each 16-channel shank yielded ~1.6 Terabytes of data for that period, and these data were divided into 10 segments of 24-hr length and clustered using MountainSort (Chung et al., 2017). Subsequently, clusters were linked across segments using a conservative mutual nearest-neighbor rule (see FIG. 7, Panels A-B).

Figure 6:
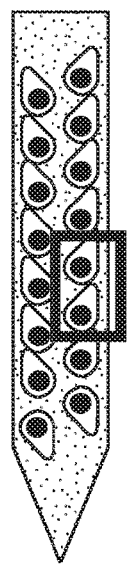
FIG. 6, Panels A-J depict the tracking of individual single-units over time.
Figure 6:
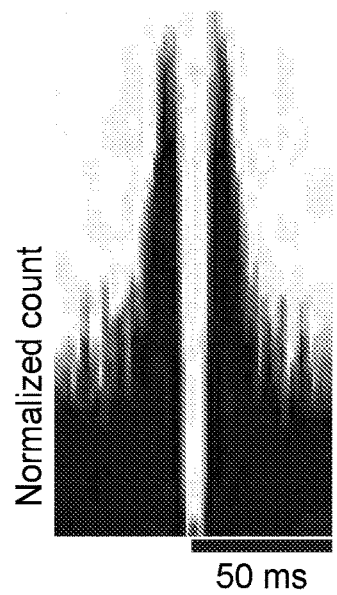
Figure 6:
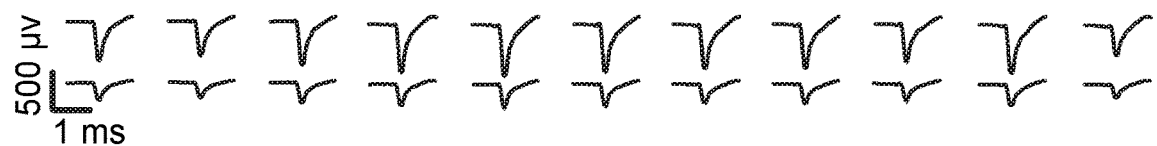
Figure 6:
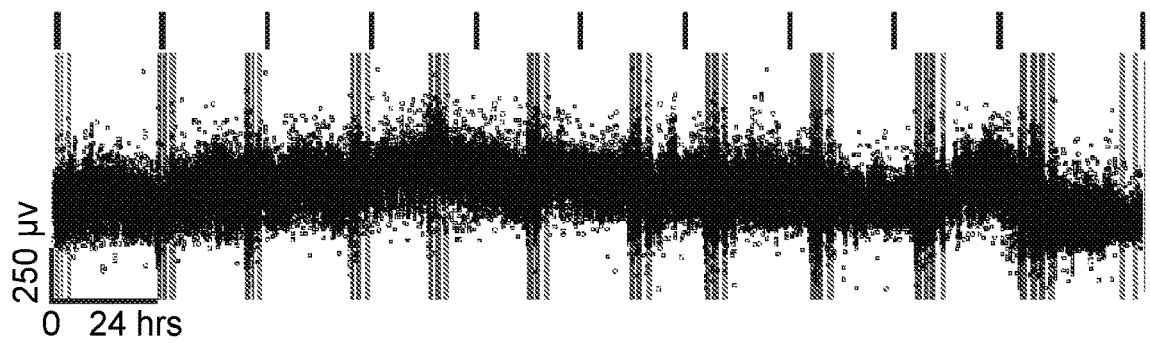
Figure 6:
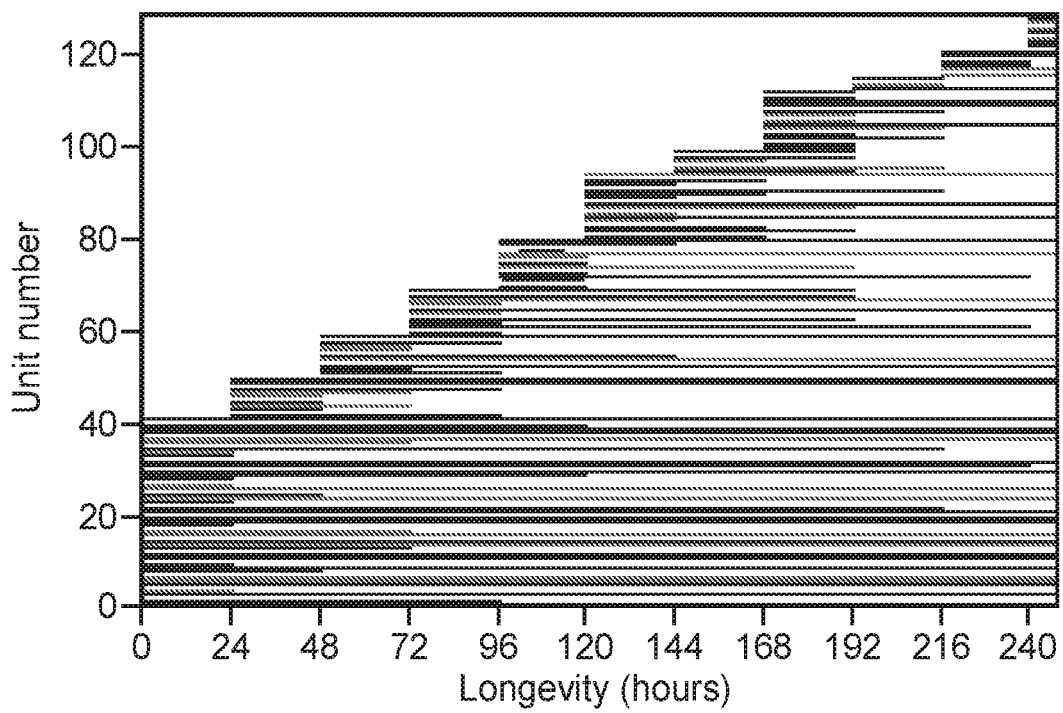
Figure 6:
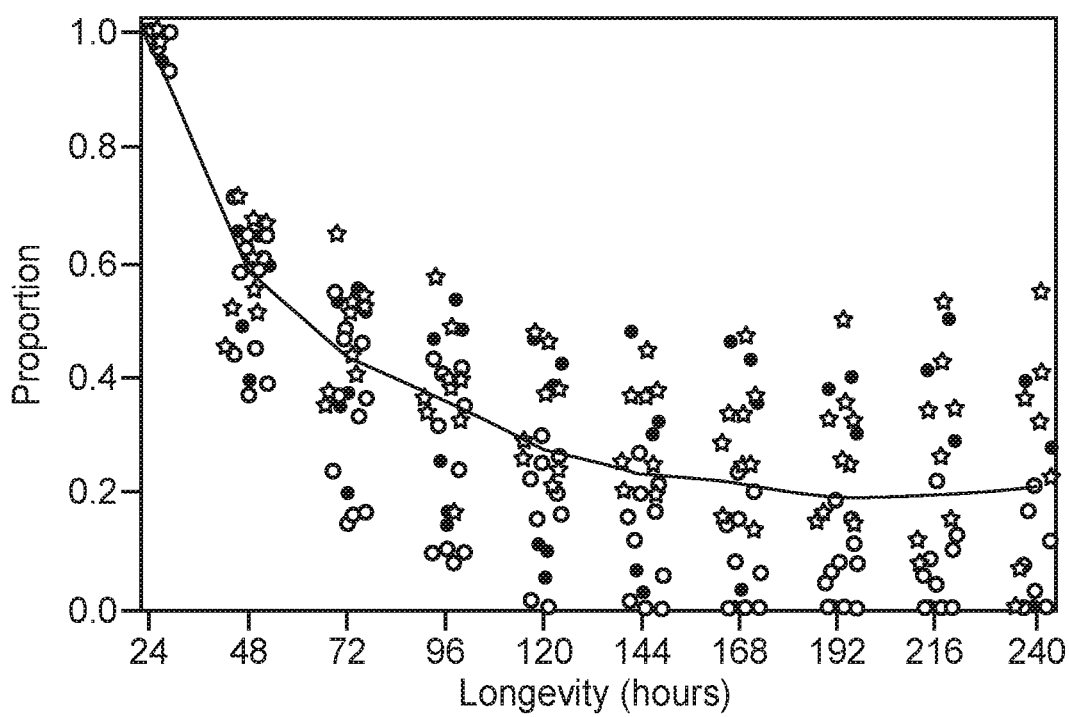
Figure 6:
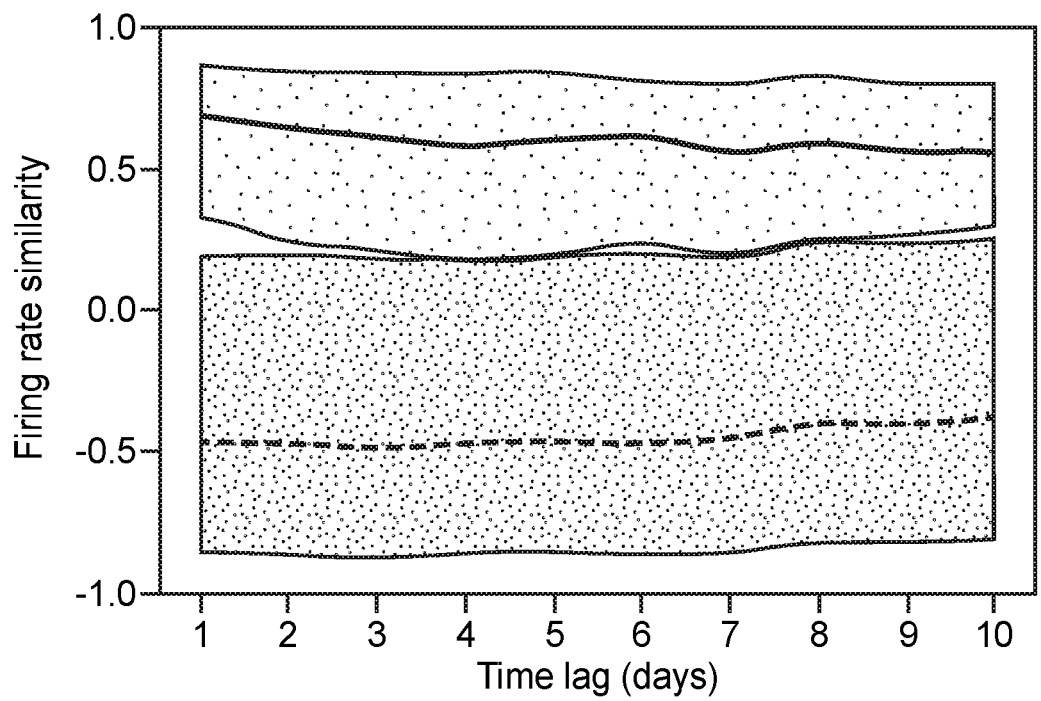
Figure 6:
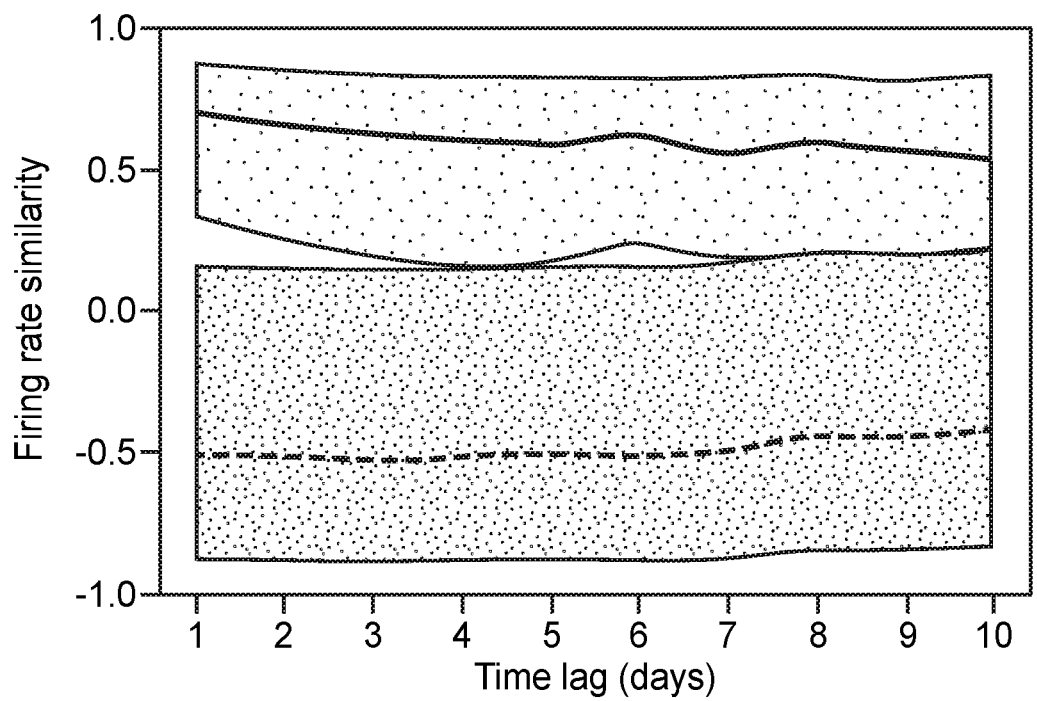
Figure 6:
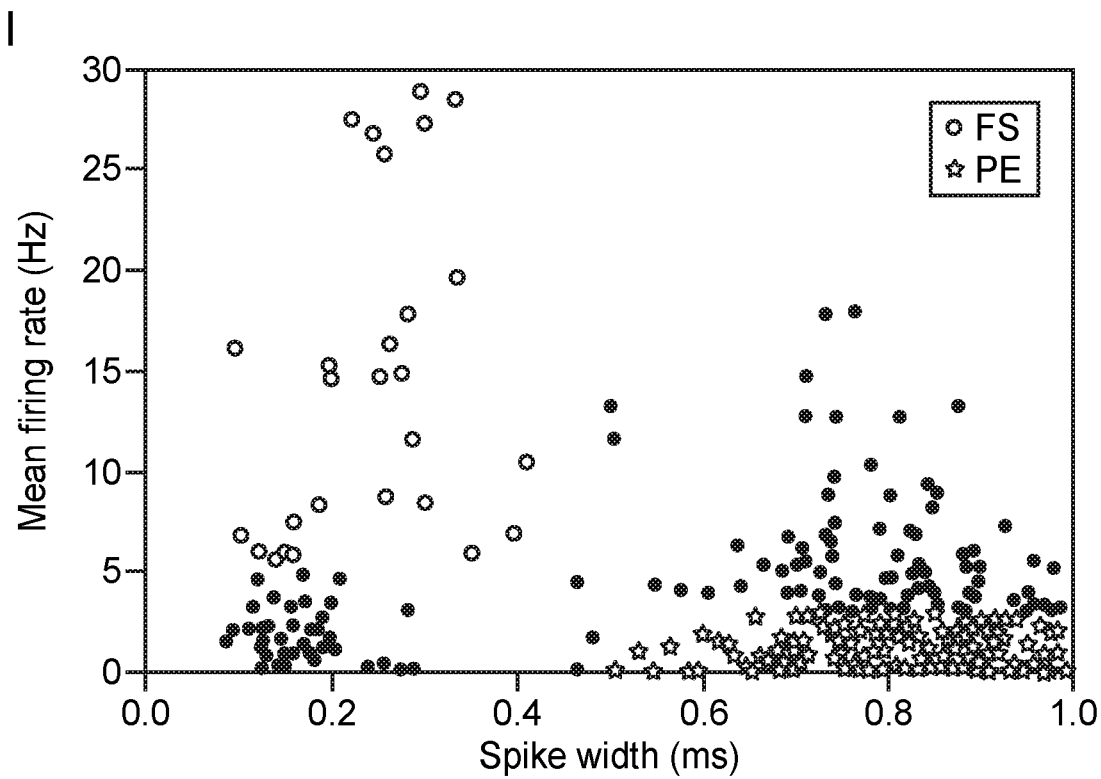
Figure 6:
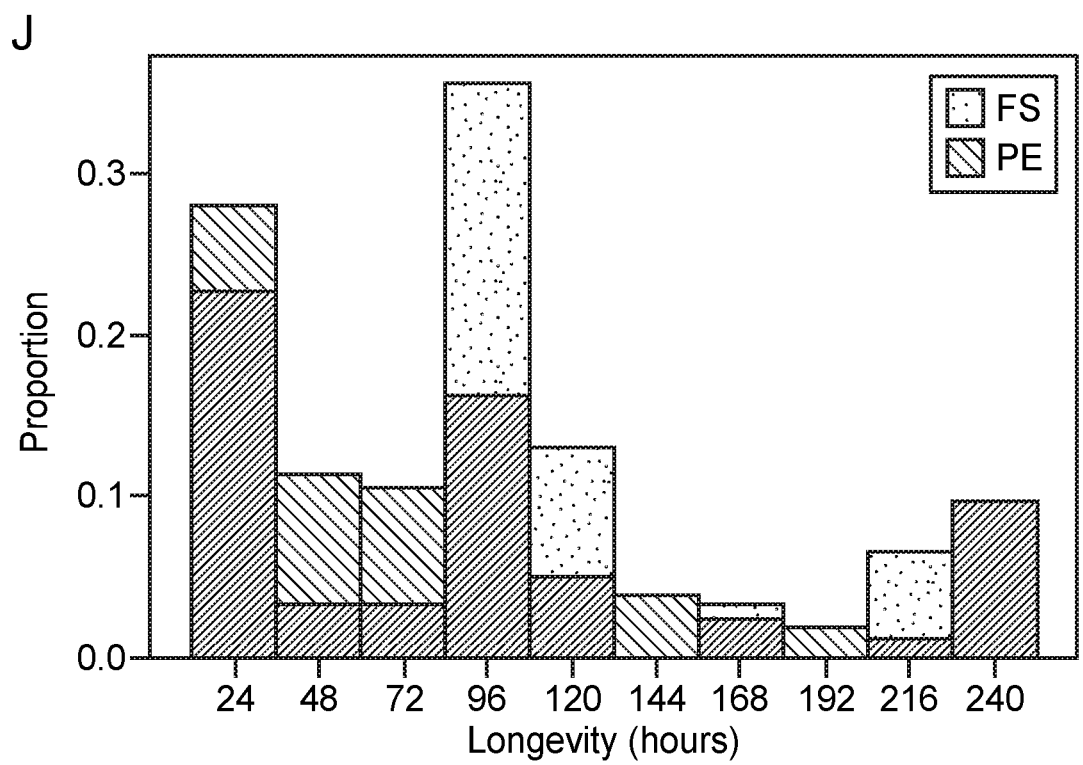

This approach enabled the identification of 2322 single units from these recordings, each of which could be clustered for at least one 24-hour periods. Moreover, a substantial fraction of these units was continuously tracked across many days, despite the expected waveform variation (Dhawale et al., 2017). An example of a unit that was tracked for the entire period was shown in FIG. 6, Panels A-D, and on this shank, 24 of 41 clusters identified in the first 24-hour segment were tracked for more than one week of recording (FIG. 6, Panel E). Of the 36 implanted shanks, 26 had at least one clustered unit (9 shanks from animal A, 6 animal B, 11 animal C). The remaining shanks had less-than-ideal signal resulting from, e.g., errors in targeting with shanks being too superficial (2 shanks animal A, 2 shanks animal B, 1 shank animal C), hardware failures (physical connector breakage in stack disconnecting 4 shanks in animal B), and one case of channels being shorted together (1 shank animal A, otherwise unknown cause).

Long term stability was quantified by focusing on the earlier days of the recordings where there was potential to track single units continuously for 7 or more days. Of the 1150 units clustered on those days, 21% (247/1150) could be tracked for 7 days of recording or more (FIG. 6, Panel F and FIG. 7, Panels C-D). This included 247 unique units from the 416 channels of recording (26 shanks with 16 channels each), or 0.59 unique units trackable for 7 days or more per channel, yielding a dataset from these three animals that permitted an in-depth analysis of long-timescale changes in single unit activity.

FIG. 6, Panels A-D depict an example unit tracked for 248 hours of continuous recording. FIG. 6, Panel A depicts a geometric layout of recording channels, with 2 boxed channels on which the unit was detected. FIG. 6, Panel B depicts average waveforms (bandpass filtered 300-6000 Hz) for the two channels indicated in FIG. 6, Panel A, calculated for 1-hour time bins every 24 hours, except for the last bin, which corresponds to the last hour of recording (hour 247 to 248). Scale bar corresponds to 500 μv and 1 ms. FIG. 6, Panel C depicts autocorrelogram for the unit, calculated over all 248 hours. X-axis corresponds to ±50 ms in 0.5 ms bins, y-axis normalized to largest bin. FIG. 6, Panel D depicts spike amplitude (bandpass filtered 300-6000 Hz) over length of continuous recording, for all ~700,000 events in the time period. Each event is shown as a black square, allowing all outliers to be seen. Black lines (FIG. 6, Panel D, top) correspond to the 1-hour bins from which average waveforms in FIG. 6, Panel B are calculated. Shading corresponds to spatial behavioral task performance either in room A (blue), or room B (red). Non-shaded times correspond to periods when the animal was either in the rest box or its home cage. FIG. 6, Panel E depicts a period over which each unit could be tracked for one shank. (See FIG. 7, Panels A-E for all other shanks). FIG. 6, Panel F depicts a proportion of units that could be tracked for a given length of time. Black is the total across 26 shanks. Each point corresponds to an individual shank from animal A (blue, 11 shanks), animal B (cyan, 6 shanks), or animal C (red, 9 shanks), jittered in the x-dimension for ease of visualization. FIG. 6, Panel G depicts median within-unit firing rate similarity ±1 quartile (shading between 25th and 75th percentiles) for all 3 animals (dark blue), calculated during behavioral task performance in room one for low velocity times (<4 cm/s) alongside the median of all between-unit time lagged similarities ±1 quartile (shading between 25th and 75th percentiles), matched for shank and time-lag (grey). FIG. 6, Panel H depicts the median within-unit firing rate similarity as in FIG. 6, Panel G, but for high velocity times (>4 cm/s). Within-unit firing rate similarity in light blue and between-unit time lagged similarities in grey. FIG. 6, Panel I depicts spike width and mean firing rate for all units in the first hour of recording. Fast-spiking (FS) units are shown in red, defined by mean firing rates >5 Hz and spike widths <0.5 ms. Putative excitatory (PE) units are shown in blue, defined by mean firing rates <3 Hz and spike widths >0.5 ms. All other units are shown in black. FIG. 6, Panel J depicts histogram of FS units (red) and PE units (blue) showing number of hours that units could be tracked.

FIG. 7, Panel A depicts a distribution of normalized distances between linked clusters. If the clusters from each segment were drifting to a greater degree than the separation between clusters, the mutual nearest neighbor cluster pairs could occur in a crowded feature space, with unlinked clusters lying close to the linked cluster. This would generate an environment where erroneous linkages could be made, causing an overestimation of how stable clusters were. To validate that the linkages between 24-hour segments were occurring in cases where the mutual nearest neighbors were unambiguous, the distances between linked cluster template to all other possible linking cluster templates (n=315,804), normalized by the distance between the two linked cluster templates (n=4,298) were calculated. Shown is a histogram of these distances, where the vertical red line marks unity, the distance of all linked cluster templates. Over 99% of all other possible linking templates lie to the right of the vertical black line (2.6 times the distance to the linked template). FIG. 7, Panel B depicts a distribution of within and between cluster normalized waveform distances. When a cluster is stable, the variability of the events should be larger than the change in the template over time. To confirm that the clusters being linked fell within the variability of events around the cluster, the cluster pair distances were normalized by the mean distance of the last 100 events in a cluster from its template ("event distance" as described herein). Shown is a histogram of distances as in FIG. 7, Panel A, with distances between linked cluster templates (red, n=4,298), and linked cluster to unlinked cluster templates (black, n=315,804), but instead normalized by the average distance of the last 100 events from their template. Over 99% of all other possible linking templates lie to the right of the vertical dotted black line (0.16), while 95% of linkage distances lie to the left of the vertical dotted red line (0.14). The distance between linked cluster templates was less than their respective within cluster event distances in all but one case (4,297 of 4,298). FIG. 7, Panel C depicts event amplitudes (bandpass filtered 300-6000 Hz) over time for the largest unit clustered on channels 1 through 4 from the shank shown in FIG. 6, Panel E. For each channel, the upper plot is from the first 24-hour period, with scalebar representing 1 hour (x-axis) and 250 μv (y-axis). For each channel, the lower plot is from the entire 248 hour recording period, with expanded 24-hour time period above shown in grey and with scalebar representing 24 hours (x-axis) and 250 μv (y-axis). All scalebars are placed at 0 hours, 0 μv. FIG. 7, Panel D depicts a period over which each cluster could be tracked, separated by inset shank id. FIG. 7, Panel E, left depicts firing rates of clusters from four shanks of animal C while performing the spatial behavioral task in room A during high velocity times (>4 cm/s). FIG. 7, Panel E, right depicts firing rate similarities at different time lags, calculated from firings rates shown to the left, from four shanks of animal C while performing the spatial behavioral task in room A at high velocity times (>4 cm/s, right). Median within-unit firing rate similarity ±1 quartile is shown in blue (shading between 25th and 75th percentiles), and median of all between-unit time lagged similarities matched for shank and time-lag, ±1 quartile in grey (shading between 25th and 75th percentiles).

Example 6: Firing Rate Stability in a Well-Learned Task

In the absence of external perturbations, the majority of single-neurons showed stable responses when measured intermittently across days. Similar observations were made from daily recordings in rodent mPFC during spatial behaviors from 60 units across 2 days, and 8 units across 6 days, suggesting that rodent mPFC units showed stable firing properties in the context of well-learned behaviors. One goal was therefore to validate the recording and automated drift tracking methods in comparison to previous findings for rodent mPFC, and to determine whether the observed stability could be confirmed with continuous recordings over longer timescales with a much larger dataset (247 mPFC units followed for a week or more).

Mean firing rates were determined. Units displayed a large range and diversity of firing rates throughout a day. Times where behavior was similar across days were observed, and therefore periods when the subjects were performing a well-learned spatial behavior in a familiar environment were observed. The behavioral states were further subdivided into times when the animal was at low (<4.0 cm/s) and high (>4.0 cm/s) speeds, as these were known to correspond to different neural states. For each unit, firing rates were calculated during these times across all ten (n=2 rats) or eleven (n=1 rat) days of continuous recording. Given the large diversity of firing rates between neurons, observing stable single-unit firing rates could only occur if both single-unit physiologic firing rates were stable and the method correctly identified individual cells across time (note here that the spike sorting methodology did not use rate or timing information).

The findings both validated the unit tracking and confirmed that firing rates taken from similar behavioral epochs show remarkable degrees of stability across many days (see FIG. 7, Panel E for data from one example animal). Stability using firing rate similarity was quantified at increasing time lags. The distribution of firing rate similarities of all units that could be tracked for multiple days was compared to the distribution of firing rate similarities for every different cluster pair (i.e. cluster pairs with different cluster ID's), recorded on the same shank, at the same time lag (see FIG. 7, Panel E for firing rate similarities for data from one animal). These analyses confirmed that units' firing rates were more similar within the same unit than between units across all days of recording for all 3 animals individually (all two-sided Wilcoxon rank sum $p<1.0e-15$ low velocity; $p<1.0e-14$, high velocity), and together (FIG. 6, Panels G-H, all two-sided Wilcoxon rank sum $p<1.0e-48$, low velocity; $p<1.0e-44$, high velocity).

Example 7: Putative Cell Type and Tracking Length

Since brain networks are made up of interacting populations of excitatory and inhibitory neurons, it was examined whether the tracked units across long timescales extended to both fast-spiking putative interneurons as well as putative excitatory cells. An approach to differentiating these unit types was via a combination of waveform shape and mean firing rate. To determine whether spike and firing rate features interacted with long term tracking, a mean firing rate and spike width (calculated as peak-to-trough time) were calculated for the first hour of data collected in the 26-shank 10-day dataset.

An examination of the relationship between these features revealed a broad distribution of values (FIG. 6, Panel I). The two extrema of the joint distribution were examined to enable a clear comparison of firing features and tracking, identifying units with firing mean firing rates >5 Hz and spike widths <0.5 ms as fast-spiking (FS) and units with firing rates <3 Hz and spike widths >0.5 ms as putative excitatory (PE). To eliminate any ambiguity in this classification, all other units that did not fit either criterion were excluded. This resulted in identification of 31 putative interneurons and 268 putative non-interneurons (FIG. 6, Panel I).

The length of time each putative cell type could be tracked was compared to each other and found that putative interneurons could be tracked for a mean time of 109 hours while putative non-interneurons could be tracked for a mean time of 105 hours (FIG. 6, Panel J), with no statistically significant difference between the two groups (two-sided Wilcoxon rank sum $p=0.13$). These findings suggested that the system did not have systematic biases in the tracking of units with different waveform and firing rate features.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

Felix, S. H., Shah, K. G., Tolosa, V. M., Sheth, H. J., Tooker, A. C., Delima, T. L., Jadhav, S. P., Frank, L. M., and Pannu, S. S. (2013). Insertion of flexible neural probes using rigid stiffeners attached with biodissolvable adhesive. Journal of visualized experiments: JoVE, e50609.

Le Guehennec, L., Soueidan, A., Layrolle, P., and Amouriq, Y. (2007). Surface treatments of titanium dental implants for rapid osseointegration. Dent Mater 23, 844-854.

Ludwig, K. A., Uram, J. D., Yang, J., Martin, D. C., and Kipke, D. R. (2006). Chronic neural recordings using silicon microelectrode arrays electrochemically deposited with a poly(3,4-ethylenedioxythiophene) (PEDOT) film. J Neural Eng 3, 59-70.

Matsumura, H., and Nakabayashi, N. (1988). Adhesive 4-META/MMA-TBB opaque resin with poly(methyl methacrylate)-coated titanium dioxide. J Dent Res 67, 29-32.

Alexander, G. M., Rogan, S. C., Abbas, A. I., Armbruster, B. N., Pei, Y., Allen, J. A., Nonneman, R. J., Hartmann, J., Moy, S. S., Nicolelis, M. A., et al. (2009). Remote control of neuronal activity in transgenic mice expressing evolved G protein-coupled receptors. Neuron 63, 27-39.

Bartho, P., Hirase, H., Monconduit, L., Zugaro, M., Harris, K. D., and Buzsaki, G. (2004). Characterization of neocortical principal cells and interneurons by network interactions and extracellular features. J Neurophysiol 92, 600-608.

Buzsaki, G. (2004). Large-scale recording of neuronal ensembles. Nat. Neurosci. 7, 446-451.

Buzsaki, G. (2015). Hippocampal sharp wave-ripple: A cognitive biomarker for episodic memory and planning. Hippocampus 25, 1073-1188.

Chen, T. W., Wardill, T. J., Sun, Y., Pulver, S. R., Renninger, S. L., Baohan, A., Schreiter, E. R., Kerr, R. A., Orger, M. B., Jayaraman, V., et al. (2013). Ultrasensitive fluorescent proteins for imaging neuronal activity. Nature 499, 295-300.

Cheng, S., and Frank, L. M. (2008). New experiences enhance coordinated neural activity in the hippocampus. Neuron 57, 303-313.

Chrobak, J. J., and Buzsaki, G. (1996). High-frequency oscillations in the output networks of the hippocampal-entorhinal axis of the freely behaving rat. J Neurosci 16, 3056-3066.

Chung, J. E., Magland, J. F., Barnett, A. H., Tolosa, V. M., Tooker, A. C., Lee, K. Y., Shah, K. G., Felix, S. H., Frank, L. M., and Greengard, L. F. (2017). A Fully Automated Approach to Spike Sorting. Neuron 95, 1381-1394 e1386.

Dhawale, A. K., Poddar, R., Wolff, S. B., Normand, V. A., Kopelowitz, E., and Olveczky, B. P. (2017). Automated long-term recording and analysis of neural activity in behaving animals. eLife 6.

Dragoi, G., Carpi, D., Recce, M., Csicsvari, J., and Buzsaki, G. (1999). Interactions between hippocampus and medial septum during sharp waves and theta oscillation in the behaving rat. J Neurosci 19, 6191-6199.

Felix, S. H., Shah, K. G., Tolosa, V. M., Sheth, H. J., Tooker, A. C., Delima, T. L., Jadhav, S. P., Frank, L. M., and Pannu, S. S. (2013). Insertion of flexible neural probes using rigid stiffeners attached with biodissolvable adhesive. J Vis Exp, e50609.

Gilletti, A., and Muthuswamy, J. (2006). Brain micromotion around implants in the rodent somatosensory cortex. J Neural Eng 3, 189-195.

Gray, C. M., Maldonado, P. E., Wilson, M., and McNaughton, B. (1995). Tetrodes markedly improve the reliability and yield of multiple single-unit isolation from multi-unit recordings in cat striate cortex. J Neurosci Methods 63, 43-54.

Greenberg, P. A., and Wilson, F. A. (2004). Functional stability of dorsolateral prefrontal neurons. J Neurophysiol 92, 1042-1055.

Hengen, K. B., Lambo, M. E., Van Hooser, S. D., Katz, D. B., and Turrigiano, G. G. (2013). Firing rate homeostasis in visual cortex of freely behaving rodents. Neuron 80, 335-342.

Hengen, K. B., Torrado Pacheco, A., McGregor, J. N., Van Hooser, S. D., and Turrigiano, G. G. (2016). Neuronal Firing Rate Homeostasis Is Inhibited by Sleep and Promoted by Wake. Cell 165, 180-191.

Herbawi, A. S., Kiessner, L., Paul, O., and Ruther, P. (2017). High-Density Cmos Neural Probe Implementing a Hierarchical Addressing Scheme for 1600 Recording Sites and 32 Output Channels. 2017 19th International Conference on Solid-State Sensors, Actuators and Microsystems (Transducers), 20-23.

Hromadka, T., Deweese, M. R., and Zador, A. M. (2008). Sparse representation of sounds in the unanesthetized auditory cortex. PLoS Biol 6, e16.

Isomura, Y., Sirota, A., Ozen, S., Montgomery, S., Mizuseki, K., Henze, D. A., and Buzsaki, G. (2006). Integration and segregation of activity in entorhinal-hippocampal subregions by neocortical slow oscillations. Neuron 52, 871-882.

Jadhav, S. P., Rothschild, G., Roumis, D. K., and Frank, L. M. (2016). Coordinated Excitation and Inhibition of Prefrontal Ensembles during Awake Hippocampal Sharp-Wave Ripple Events. Neuron 90, 113-127.

Jeong, J. W., Shin, G., Park, S. I., Yu, K. J., Xu, L., and Rogers, J. A. (2015). Soft materials in neuroengineering for hard problems in neuroscience. Neuron 86, 175-186.

Ji, D., and Wilson, M. A. (2007). Coordinated memory replay in the visual cortex and hippocampus during sleep. Nat Neurosci 10, 100-107.

Jun, J. J., Steinmetz, N. A., Siegle, J. H., Denman, D. J., Bauza, M., Barbarits, B., Lee, A. K., Anastassiou, C. A., Andrei, A., Aydin, C., et al. (2017). Fully integrated silicon probes for high-density recording of neural activity. Nature 551, 232-236.

Kay, K., Sosa, M., Chung, J. E., Karlsson, M. P., Larkin, M. C., and Frank, L. M. (2016). A hippocampal network for spatial coding during immobility and sleep. Nature 531, 185-190.

Khodagholy, D., Gelinas, J. N., and Buzsaki, G. (2017). Learning-enhanced coupling between ripple oscillations in association cortices and hippocampus. Science 358, 369-372.

Kim, T. I., McCall, J. G., Jung, Y. H., Huang, X., Siuda, E. R., Li, Y., Song, J., Song, Y. M., Pao, H. A., Kim, R. H., et al. (2013). Injectable, cellular-scale optoelectronics with applications for wireless optogenetics. Science 340, 211-216.

Kuo, J. T., Kim, B. J., Hara, S. A., Lee, C. D., Gutierrez, C. A., Hoang, T. Q., and Meng, E. (2013). Novel flexible Parylene neural probe with 3D sheath structure for enhancing tissue integration. Lab Chip 13, 554-561.

Lansink, C. S., Goltstein, P. M., Lankelma, J. V., McNaughton, B. L., and Pennartz, C. M. (2009). Hippocampus leads ventral striatum in replay of place-reward information. PLoS Biol 7, e1000173.

Le Guehennec, L., Soueidan, A., Layrolle, P., and Amouriq, Y. (2007). Surface treatments of titanium dental implants for rapid osseointegration. Dent Mater 23, 844-854.

Lee, H. C., Ejserholm, F., Gaire, J., Currlin, S., Schouenborg, J., Wallman, L., Bengtsson, M., Park, K., and Otto, K. J. (2017a). Histological evaluation of flexible neural implants; flexibility limit for reducing the tissue response? J Neural Eng 14, 036026.

Lee, H. C., Gaire, J., Roysam, B., and Otto, K. J. (2017b). Placing Sites on the Edge of Planar Silicon Microelectrodes Enhances Chronic Recording Functionality. IEEE Trans Biomed Eng.

Li, B. Z., Lee, K., Masmanidis, S. C., and Li, M. (2018). A nanofabricated optoelectronic probe for manipulating and recording neural dynamics. J Neural Eng 15.

Logothetis, N. K., Eschenko, O., Murayama, Y, Augath, M., Steudel, T., Evrard, H. C., Besserve, M., and Oeltermann, A. (2012). Hippocampal-cortical interaction during periods of subcortical silence. Nature 491, 547-553.

Lopez, C. M., Putzeys, J., Raducanu, B. C., Ballini, M., Wang, S. W., Andrei, A., Rochus, V., Vandebriel, R., Severi, S., Van Hoof, C., et al. (2017). A Neural Probe With Up to 966 Electrodes and Up to 384 Configurable Channels in 0.13 mu m SOI CMOS. Ieee T Biomed Circ S 11, 510-522.

Luan, L., Wei, X. L., Zhao, Z. T., Siegel, J. J., Potnis, O., Tuppen, C. A., Lin, S. Q., Kazmi, S., Fowler, R. A., Holloway, S., et al. (2017). Ultraflexible nanoelectronic probes form reliable, glial scar-free neural integration. Sci Adv 3.

Ludwig, K. A., Uram, J. D., Yang, J., Martin, D. C., and Kipke, D. R. (2006). Chronic neural recordings using silicon microelectrode arrays electrochemically deposited with a poly(3,4-ethylenedioxythiophene) (PEDOT) film. J Neural Eng 3, 59-70.

Matsumura, H., and Nakabayashi, N. (1988). Adhesive 4-META/MMA-TBB opaque resin with poly(methyl methacrylate)-coated titanium dioxide. J Dent Res 67, 29-32.

McMahon, D. B., Jones, A. P., Bondar, I. V., and Leopold, D. A. (2014). Face-selective neurons maintain consistent visual responses across months. Proc Natl Acad Sci USA 111, 8251-8256.

Mizuseki, K., and Buzsaki, G. (2013). Preconfigured, skewed distribution of firing rates in the hippocampus and entorhinal cortex. Cell reports 4, 1010-1021.

Mols, K., Musa, S., Nuttin, B., Lagae, L., and Bonin, V. (2017). In vivo characterization of the electrophysiological and astrocytic responses to a silicon neuroprobe implanted in the mouse neocortex. Scientific reports 7, 15642.

O'Connor, D. H., Peron, S. P., Huber, D., and Svoboda, K. (2010). Neural activity in barrel cortex underlying vibrissa-based object localization in mice. Neuron 67, 1048-1061.

Pennartz, C. M., Lee, E., Verheul, J., Lipa, P., Barnes, C. A., and McNaughton, B. L. (2004). The ventral striatum in off-line processing: ensemble reactivation during sleep and modulation by hippocampal ripples. J Neurosci 24, 6446-6456.

Pfeiffer, B. E., and Foster, D. J. (2013). Hippocampal place-cell sequences depict future paths to remembered goals. Nature 497, 74-79.

Pfeiffer, B. E., and Foster, D. J. (2015). Autoassociative dynamics in the generation of sequences of hippocampal place cells. Science 349, 180-183.

Powell, N.J., and Redish, A. D. (2014). Complex neural codes in rat prelimbic cortex are stable across days on a spatial decision task. Frontiers in behavioral neuroscience 8, 120.

Raducanu, B. C., Yazicioglu, R. F., Lopez, C. M., Ballini, M., Putzeys, J., Wang, S. W., Andrei, A., Rochus, V., Welkenhuysen, M., van Helleputte, N., et al. (2017). Time Multiplexed Active Neural Probe with 1356 Parallel Recording Sites. Sensors-Basel 17.

Rodger, D. C., Fong, A. J., Wen, L., Ameri, H., Ahuja, A. K., Gutierrez, C., Lavrov, I., Hui, Z., Menon, P. R., Meng, E., et al. (2008). Flexible parylene-based multielectrode array technology for high-density neural stimulation and recording. Sensor Actuat B-Chem 132, 449-460.

Rose, T., Jaepel, J., Hubener, M., and Bonhoeffer, T. (2016). Cell-specific restoration of stimulus preference after monocular deprivation in the visual cortex. Science 352, 1319-1322.

Rothschild, G., Eban, E., and Frank, L. M. (2017). A cortical-hippocampal-cortical loop of information processing during memory consolidation. Nat Neurosci 20, 251-259.

Rudmann, L., Alt, M. T., Vajari, D. A., and Stieglitz, T. (2018). Integrated optoelectronic microprobes. Current Opinion in Neurobiology 50, 72-82.

Scholvin, J., Kinney, J. P., Bernstein, J. G., Moore-Kochlacs, C., Kopell, N., Fonstad, C. G., and Boyden, E. S. (2016). Close-Packed Silicon Microelectrodes for Scalable Spatially Oversampled Neural Recording. Ieee T Bio-Med Eng 63, 120-130.

Seo, D., Carmena, J. M., Rabaey, J. M., Maharbiz, M. M., and Alon, E. (2015). Model validation of untethered, ultrasonic neural dust motes for cortical recording. J Neurosci Methods 244, 114-122.

Seo, D., Neely, R. M., Shen, K., Singhal, U., Alon, E., Rabaey, J. M., Carmena, J. M., and Maharbiz, M. M. (2016). Wireless Recording in the Peripheral Nervous System with Ultrasonic Neural Dust. Neuron 91, 529-539.

Seymour, J. P., Wu, F., Wise, K. D., and Yoon, E. (2017). State-of-the-art MEMS and microsystem tools for brain research. Microsystems &Amp; Nanoengineering 3, 16066.

Sirota, A., Csicsvari, J., Buhl, D., and Buzsaki, G. (2003). Communication between neocortex and hippocampus during sleep in rodents. Proc Natl Acad Sci USA 100, 2065-2069.

Tang, W., Shin, J. D., Frank, L. M., and Jadhav, S. P. (2017). Hippocampal-Prefrontal Reactivation during Learning Is Stronger in Awake Compared with Sleep States. J Neurosci 37, 11789-11805.

Tooker, A., Liu, D., Anderson, E. B., Felix, S., Shah, K. G., Lee, K. Y., Chung, J. E., Pannu, S., Frank, L., and Tolosa, V. (2014). Towards a large-scale recording system: demonstration of polymer-based penetrating array for chronic neural recording. Conf Proc IEEE Eng Med Biol Soc 2014, 6830-6833.

Tooker, A., Madsen, T. E., Yorita, A., Crowell, A., Shah, K. G., Felix, S., Mayberg, H. S., Pannu, S., Rainnie, D. G., and Tolosa, V. (2013). Microfabricated Polymer-Based Neural Interface for Electrical Stimulation/Recording, Drug Delivery, and Chemical Sensing-Development. Ieee Eng Med Bio, 5159-5162.

Tooker, A., Tolosa, V., Shah, K. G., Sheth, H., Felix, S., Delima, T., and Pannu, S. (2012a). Optimization of multi-layer metal neural probe design. Conf Proc IEEE Eng Med Biol Soc 2012, 5995-5998.

Tooker, A., Tolosa, V., Shah, K. G., Sheth, H., Felix, S., Delima, T., and Pannu, S. (2012b). Polymer neural interface with dual-sided electrodes for neural stimulation and recording. Conf Proc IEEE Eng Med Biol Soc 2012, 5999-6002.

Wassum, K. M., Tolosa, V. M., Wang, J., Walker, E., Monbouquette, H. G., and Maidment, N. T. (2008). Silicon Wafer-Based Platinum Microelectrode Array Biosensor for Near Real-Time Measurement of Glutamate in Vivo. Sensors (Basel) 8, 5023-5036.

Wierzynski, C. M., Lubenov, E. V., Gu, M., and Siapas, A. G. (2009). State-dependent spike-timing relationships between hippocampal and prefrontal circuits during sleep. Neuron 61, 587-596.

Wu, F., Stark, E., Im, M., Cho, I. J., Yoon, E. S., Buzsaki, G., Wise, K. D., and Yoon, E. (2013). An implantable neural probe with monolithically integrated dielectric waveguide and recording electrodes for optogenetics applications. J Neural Eng 10, 056012.

Wu, F., Stark, E., Ku, P. C., Wise, K. D., Buzsaki, G., and Yoon, E. (2015). Monolithically Integrated muLEDs on Silicon Neural Probes for High-Resolution Optogenetic Studies in Behaving Animals. Neuron 88, 1136-1148.

Xie, C., Liu, J., Dai, X., Zhou, W., and Lieber, C. M. (2015). Three-dimensional macroporous nanoelectronic networks as minimally invasive brain probes. Nature Materials 14, 1286-1292.

Yu, J. Y., Kay, K., Liu, D. F., Grossrubatscher, I., Loback, A., Sosa, M., Chung, J. E., Karlsson, M. P., Larkin, M. C., and Frank, L. M. (2017). Distinct hippocampal-cortical memory representations for experiences associated with movement versus immobility. eLife 6.

Zhao, Z., Luan, L., Wei, X., Zhu, H., Li, X., Lin, S., Siegel, J. J., Chitwood, R. A., and Xie, C. (2017). Nanoelectronic Coating Enabled Versatile Multifunctional Neural Probes. Nano letters 17, 4588-4595.

What is claimed is:

1. A method of implanting an implantable device in contact with a brain of a subject, the method comprising:
   (a) removing a portion of a skull and a portion of an underlying dura of a subject to create an opening in the skull to expose a surface of the brain of the subject;

(b) positioning the implantable device in contact with the brain of the subject, wherein the implantable device comprises a plurality of electrodes and a measuring device;

(c) positioning a first polymeric material in contact with the surface of the brain to form a seal;

(d) positioning a second polymeric material on the first polymeric material, wherein the second polymeric material has a higher viscosity than the first polymeric material; and (e) positioning a capping element over the opening in the skull.

2. The method of claim 1, wherein the first polymeric material comprises a biocompatible material.

3. The method of claim 1, wherein the biocompatible material comprises a silicone elastomer.

4. The method of claim 1, wherein the positioning the first polymeric material further comprising providing strain relief for the positioning of the implantable device in contact with the brain of the subject.

5. The method of claim 1, wherein the positioning the first polymeric material comprises applying a pressure to the implantable device that matches intracranial pressure.

6. The method of claim 5, wherein the pressure is a downward pressure.

7. The method of claim 1, wherein the second polymeric material is biocompatible.

8. The method of claim 1, wherein the second polymeric material comprises a silicone elastomer.

9. The method of claim 1, wherein the second polymeric material comprises a harder material than the first polymeric material.

10. The method of claim 1, wherein the capping element comprises at least two materials.

11. The method of claim 10, wherein the at least two materials comprises a casing and a hard outer layer.

12. The method of claim 11, wherein the casing is a 3D-printed material.

13. The method of claim 11, wherein the hard outer layer comprises a titanium plate.

14. The method of claim 13, wherein the titanium plate is anchored to the skull.

15. The method of claim 1, wherein the positioning the implantable device in contact with the brain is on the surface of the brain.

16. The method of claim 1, wherein the positioning the implantable device in contact with the brain is within the brain under the surface of the brain.

17. The method of claim 1, wherein the plurality of electrodes are partially or substantially embedded into the second polymeric material.

18. The method of claim 1, wherein the plurality of electrodes comprises 64 channels or 1024 channels.

19. The method of claim 1, wherein the plurality of electrodes comprises a flexible polymeric material.

20. The method of claim 1, wherein the plurality of electrodes comprises one or more platinum electrodes extending across a length of the implantable device.

21. The method of claim 1, wherein the measuring device comprises a communication unit.

22. The method of claim 21, wherein the communication unit is a wireless communication unit.

23. The method of claim 22, wherein the wireless communication unit comprises Radio-frequency Identification, Bluetooth, or Near Field Communication.

24. The method of claim 1, wherein the positioning the implantable device in contact with the brain of the subject further comprising anchoring the measuring device to the surface of the brain.

25. The method of claim 24, wherein the anchoring comprising affixing the measuring device with a biocompatible material.

26. The method of claim 25, wherein the biocompatible material comprises polyimide.

27. The method of claim 1, wherein the positioning the implantable device in contact with the brain of the subject further comprising adhering the plurality of electrodes to a removable stiffener to facilitate the positioning of the implantable device.

28. The method of claim 27, wherein the removable stiffener comprises a biocompatible material.

29. The method of claim 27, wherein the removable stiffener comprises silicon.

30. The method of claim 27, wherein the adhering comprising disposing an adhesive on a top surface of the plurality of electrodes.

31. The method of claim 30, wherein the adhesive comprises polyethylene glycol.

32. The method of claim 1, wherein the method further comprising positioning an implantation device around the opening in the skull, wherein the implantation device comprises a lumen and walls, wherein the lumen provides access to the surface of the brain.

33. The method of claim 32, wherein the implantation device is placed orthogonal to the surface of the skull.

34. The method of claim 32, wherein the walls of the implantation device comprise a bottom surface, wherein the bottom surface conforms to a perimeter contour of the surface of the skull.

35. The method of claim 32, wherein the walls of the implantation device comprise a frustoconical shaped cross-section, a cylindrical shaped cross-section, a circular shaped cross-section or a rectangular shaped cross-section.

36. The method of claim 32, wherein the implantation device comprises a 3D-printed material.

37. The method of claim 32, wherein the implantation device comprises a biocompatible material.

38. The method of claim 32, wherein the implantation device comprises silicon.

39. The method of claim 32, wherein the positioning further comprising anchoring the implantation device to the skull.

40. The method of claim 39, wherein the anchoring comprising screwing the implantation device with one or more screws.

41. The method of claim 40, wherein the screws comprise titanium.

42. The method of claim 39, wherein the anchoring comprising adhering the implantation device to a surface of the skull using an adhesive disposed on a bottom surface of the walls of the implantation device in contact with the surface of the skull.

43. The method of claim 42, wherein the adhesive is methylmethacrylate with 4-methacryloyloxyethy trimellitate anhydride.

44. The method of claim 32, wherein the method further comprising removing the implantation device from the opening in the skull.

45. The method of claim 32, wherein the implantation device further comprises: a first polymeric material within the lumen; and a second polymeric material positioned on the first polymeric material, wherein the second polymeric material has a higher viscosity than the first polymeric material.

\* \* \* \* \*

UNITED STATES PATENT AND TRADEMARK OFFICE
CERTIFICATE OF CORRECTION

PATENT NO. : 11,648,394 B2
APPLICATION NO. : 16/756013
DATED : May 16, 2023
INVENTOR(S) : Loren M. Frank et al.

It is certified that error appears in the above-identified patent and that said Letters Patent is hereby corrected as shown below:

In the Specification

In Column 3, Line 38, delete "e g" and insert -- e.g. --.
In Column 6, Line 62, delete "e g," and insert -- e.g., --.
In Column 7, Line 16, delete "mm" and insert -- mm. --.
In Column 7, Line 60, delete "(ethyleneco-vinyl)" and insert -- (ethylene-co-vinyl --.
In Column 8, Line 19, delete "poly(lactideco-" and insert -- poly(lactide-co- --.
In Column 8, Line 25, delete "poly(lactideco-" and insert -- poly(lactide-co- --.
In Column 11, Line 59, delete "pentantoate" and insert -- pentanoate --.
In Column 12, Line 33, delete "4-methacryloyloxyethy" and insert -- 4-methacryloyloxyethyl --.
In Column 17, Line 7, delete "Narshige)." and insert -- Narishige). --.
In Column 17, Line 45, delete "(Quik-sil," and insert -- (Kwik-sil, --.
In Column 22, Line 43, after "C')," insert -- . . . --.
In Column 27, Line 5, delete "Wilicoxon" and insert -- Wilcoxon --.

In the Claims

In Column 38, Line 60, delete "4-methacryloyloxyethy" and insert -- 4-methacryloyloxyethyl --.

Signed and Sealed this
Fifteenth Day of July, 2025

Coke Morgan Stewart
*Acting Director of the United States Patent and Trademark Office*